US009902961B2

(12) United States Patent
Dausse et al.

(10) Patent No.: US 9,902,961 B2
(45) Date of Patent: Feb. 27, 2018

(54) APTAMERS INHIBITING THE ENZYMATIC ACTIVITY OF THE MMP-9 PROTEIN

(71) Applicants: L V M H Recherche, Saint Jean de Braye (FR); Institut National de la Santé et de la Recherche Médicale (INSERM), Paris (FR)

(72) Inventors: Eric Dausse, Bordeaux (FR); Jean-Jacques Toulme, Lormont (FR); Jean Hubert Cauchard, Orleans (FR); Robin Kurfurst, Saint Jean de Braye (FR); Sylvianne Schnebert, Olivet (FR)

(73) Assignees: LVMH Recherche, Saint Jean de Brave (FR); Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 15/108,681

(22) PCT Filed: Dec. 30, 2014

(86) PCT No.: PCT/EP2014/079471
§ 371 (c)(1),
(2) Date: Jun. 28, 2016

(87) PCT Pub. No.: WO2015/101637
PCT Pub. Date: Jul. 9, 2015

(65) Prior Publication Data
US 2016/0326530 A1 Nov. 10, 2016

(30) Foreign Application Priority Data
Dec. 30, 2013 (FR) ...................... 13 63696

(51) Int. Cl.
*C12N 15/11* (2006.01)
*C12N 15/115* (2010.01)
*A61Q 19/08* (2006.01)
*A61K 8/60* (2006.01)
*A61Q 19/00* (2006.01)
*A61Q 17/04* (2006.01)
*A61Q 19/02* (2006.01)
*A61Q 19/10* (2006.01)
*C12N 15/10* (2006.01)

(52) U.S. Cl.
CPC ............ *C12N 15/115* (2013.01); *A61K 8/606* (2013.01); *A61Q 17/04* (2013.01); *A61Q 19/00* (2013.01); *A61Q 19/02* (2013.01); *A61Q 19/08* (2013.01); *A61Q 19/10* (2013.01); *C12N 15/1048* (2013.01); *C12Y 304/24035* (2013.01); *A61K 2800/782* (2013.01); *C12N 2310/16* (2013.01); *C12N 2320/30* (2013.01); *C12N 2320/51* (2013.01)

(58) Field of Classification Search
None
See application file for complete search history.

(56) References Cited

U.S. PATENT DOCUMENTS

| | | | | | |
|---|---|---|---|---|---|
| 5,756,291 | A | * | 5/1998 | Griffin | C12N 9/6429 435/6.1 |
| 2009/0311245 | A1 | * | 12/2009 | Devy | C07K 16/40 424/130.1 |
| 2009/0318511 | A1 | * | 12/2009 | Leutert | C07C 311/19 514/357 |
| 2012/0244536 | A1 | * | 9/2012 | Shuber | G01N 33/5308 435/6.11 |
| 2015/0353932 | A1 | * | 12/2015 | Jackson | C12N 15/115 536/23.1 |

FOREIGN PATENT DOCUMENTS

WO WO 2010/110914 9/2010
WO WO 2013/153138 10/2013

OTHER PUBLICATIONS

Gomes et al, 99mTc-MAG3-Aptamer for Imaging Human Tumors Associated with High Level of Matrix Metalloprotease-9, 2012, Bioconjugate Chemistry, 23: 2192-2200.*
Bertini et al., *Combining in Silico Tools and NMR Data to Validate Protein-Ligand Structural Models: Application to Matrix Metalloprteinases*, 48 J. Med. Chem. 7544-7559 (2005).
Chaussain-Miller et al., *The Role of Matrix Metalloproteinases (MMPs) in Human Caries*, 85(1) J. Dent. Res. 22-32 (2006).
Folgueras et al., *Matrix metalloproteinases in cancer: from new functions to improved inhibition strategies*, 48 Int. J. Dev. Bio. 411-424 (2004).
Gatto et al., *Nucleic Acid Aptamers Based on the G-Quadruplex Structure: Therapeutic and Diagnostic Potential*, 16 Current Medicinal Chemistry 1248-1265 (2009).
Da Rocha Gomes et al., $^{99m}Tc$-*MAG3-Aptamer for Imaging Human Tumors Associated with High Level of Matrix Metalloprotease-9*, 23 Bioconjugate Chem. 2192-2200 (2012).
Gu et al., *A Highly Specific Inhibitor of Matrix Metalloproteinase-9 Rescues Laminin from Proteolysis and Neurons from Apoptosis in Transient Focal Cerebral Ischemia*, 25(27) The Journal of Neuroscience 6401-6408 (Jul. 6, 2005).
Inomata et al., *Possible Involvement of Gelatinases in Basement Membrane Damage and Wrinkle Formation in Chronically Ultraviolet B-exposed Hairless Mouse*, 120(1) The Journal of Investigative Dermatology 1-7 (2003).
C.G. Knight, *A quenched fluorescent substrate for thimet peptidase containing a new fluorescent amino acid, DL-2-amino-3-(7-methoxy-4-coumaryl)propionic acid*, 45 Biochem. J. 45-48 (1991).
Knight et al., *A novel coumarin-labelled peptide for sensitive continuous assays of the matrix metalloproteinases*, 296(3) FEBS 263-266 (Jan. 1992).

(Continued)

*Primary Examiner* — Ekaterina Poliakova-Georgantas
(74) *Attorney, Agent, or Firm* — Buchanan Ingersoll & Rooney PC

(57) ABSTRACT

The invention relates to an aptamer that has a G-quadruplex structure and is able to inhibit the enzymatic activity of the MMP-9 protein, as well as to the dermatological and cosmetic uses thereof.

14 Claims, 6 Drawing Sheets

(56) References Cited

OTHER PUBLICATIONS

Lateef et al., *All*-trans-*Retinoic Acid Supresses Matrix Metalloproteinase Activity and Increases Collagen Synthesis in Diabetic Human Skin in Organ Culture*, 165(1) American Journal of Pathology 167-174 (Jul. 2004).

Sundquist et al., *Telomeric DNA dimerizes by formation of guanine tetrads between hairpin loops*, 342 Nature 825-829 (Dec. 14, 1989).

Tucker et al., *G-quadruplex DNA Aptamers and their Ligands: Structure, Function and Application*, 18 Current Pharmaceutical Design 2014-2026 (2012).

Williams et al., *PCR product with strands of unequal length*, 23(20) Nucleic Acids Research 4220-4221 (1995).

Williamson et al., *Monovalent Cation-Induced Structure of Telomeric DNA: The G-Quartet Model*, 59 Cell 871-880 (Dec. 1, 1989).

\* cited by examiner

Figure 1

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| 11F46  | T | C | G | A | A | T | T | G | G | G | T | T | G | G | G | T | C | C | G | G | C | T | C | C | C | T | T | | | |
| 11F46A | T | C | G | A | A | T | T | G | G | G | T | T | G | G | G | T | C | C | G | G | C | T | C | C | C | T | T | | | |
| 11F46B | T | C | G | A | A | T | T | G | G | G | T | T | G | G | G | T | C | C | G | G | C | T | C | C | C | T | T | | | |
| 11F46C | T | C | G | A | A | T | T | G | G | G | T | T | G | G | G | T | C | C | G | G | C | T | C | C | C | T | T | | | |
| 8F14A  | T | C | G | A | A | T | C | G | T | A | T | G | G | G | A | C | C | G | G | T | G | T | T | G | G | C | C | T | G | A | G | C |
| 8F14B  | T | C | G | A | A | T | C | G | T | A | T | G | G | G | A | C | C | G | G | T | G | T | T | G | G | C | C | T | G | A | G | C |
| 8F14C  | T | C | G | A | A | T | C | G | T | A | T | G | G | G | A | C | C | G | G | T | G | T | T | G | G | C | C | T | G | A | G | C |
| 8F27A  | T | C | G | A | A | C | C | G | A | G | G | T | T | G | G | A | C | T | T | C | G | C | C | C | T | C | G | G | T | G | A | G | C |
| 8F27B  | T | C | G | A | A | C | C | G | A | G | G | T | T | G | G | A | C | T | T | C | G | C | C | C | T | C | G | G | T | G | A | G | C |

SEQUENCE LISTING

```
<160> NUMBER OF SEQ ID NOS: 61

<210> SEQ ID NO 1
<211> LENGTH: 27
<212> TYPE: DNA
<213> ORGANISM: artificial
<220> FEATURE:
<223> OTHER INFORMATION: Consensus sequence of group I anti-MMP9 aptamer
<220> FEATURE:
<221> NAME/KEY: misc_feature
<222> LOCATION: (1)..(4)
<223> OTHER INFORMATION: n stands for 0 or 1 G nucleotide
<220> FEATURE:
<221> NAME/KEY: misc_feature
<222> LOCATION: (26)..(27)
<223> OTHER INFORMATION: n stands for 0 or 1 G nucleotide

<400> SEQUENCE: 1
nnnntttggt gggtytgggg twgyknn                                     27

<210> SEQ ID NO 2
<211> LENGTH: 23
<212> TYPE: DNA
<213> ORGANISM: artificial
<220> FEATURE:
<223> OTHER INFORMATION: Consensus sequence of group II anti-MMP9
      aptamer

<400> SEQUENCE: 2
tggcrcgggg ttggtgtygg gtt                                         23

<210> SEQ ID NO 3
<211> LENGTH: 24
<212> TYPE: DNA
<213> ORGANISM: artificial
<220> FEATURE:
<223> OTHER INFORMATION: Consensus sequence of group III anti-MMP
      aptamer
<220> FEATURE:
<221> NAME/KEY: misc_feature
<222> LOCATION: (12)..(12)
<223> OTHER INFORMATION: n stands for 0 or 1 A nucleotide

<400> SEQUENCE: 3
gggwttggct tncggygcct ggcg                                        24

<210> SEQ ID NO 4
<211> LENGTH: 21
<212> TYPE: DNA
<213> ORGANISM: artificial
<220> FEATURE:
<223> OTHER INFORMATION: Consensus sequence of group IV anti-MMP9
      aptamer
<220> FEATURE:
<221> NAME/KEY: misc_feature
<222> LOCATION: (9)..(9)
<223> OTHER INFORMATION: n stands for 0 or 1 T nucleotide

<400> SEQUENCE: 4
gtggttggng skrtrgwkgk t                                           21
```

```
<210> SEQ ID NO 5
<211> LENGTH: 14
<212> TYPE: DNA
<213> ORGANISM: artificial
<220> FEATURE:
<223> OTHER INFORMATION: Consensus sequence of group V anti-MMP9 aptamer

<400> SEQUENCE: 5
gggtgggggg gtgg                                                       14

<210> SEQ ID NO 6
<211> LENGTH: 30
<212> TYPE: DNA
<213> ORGANISM: artificial
<220> FEATURE:
<223> OTHER INFORMATION: Consensus sequence of group VI anti-MMP9
      aptamer

<400> SEQUENCE: 6
ttggtgggat gggggggggg ttgttcggct                                      30

<210> SEQ ID NO 7
<211> LENGTH: 30
<212> TYPE: DNA
<213> ORGANISM: artificial
<220> FEATURE:
<223> OTHER INFORMATION: Consensus sequence of group VII anti-MMP9
      aptamer

<400> SEQUENCE: 7 ctggggtgt gtygcgattg tgtgggtggg                                       30

<210> SEQ ID NO 8
<211> LENGTH: 30
<212> TYPE: DNA
<213> ORGANISM: artificial
<220> FEATURE:
<223> OTHER INFORMATION: Consensus sequence of group VIII anti-MMP9
      aptamer

<400> SEQUENCE: 8
scscggtgga ytggttgggt ttggatcccc                                      30

<210> SEQ ID NO 9
<211> LENGTH: 30
<212> TYPE: DNA
<213> ORGANISM: artificial
<220> FEATURE:
<223> OTHER INFORMATION: Consensus sequence of group IX anti-MMP9
      aptamer

<400> SEQUENCE: 9
tgaggggggt ggatgggagg gttccgcacg                                      30

<210> SEQ ID NO 10
<211> LENGTH: 30
<212> TYPE: DNA
<213> ORGANISM: artificial
<220> FEATURE:
<223> OTHER INFORMATION: Consensus sequence of group X anti-MMP9 aptamer

<400> SEQUENCE: 10
tggacggtgg gttggggcgg ggggtgtcca                                      30

<210> SEQ ID NO 11
```

```
<211> LENGTH: 21
<212> TYPE: DNA
<213> ORGANISM: artificial
<220> FEATURE:
<223> OTHER INFORMATION: aptamer 11F46min

<400> SEQUENCE: 11
tttggtgggt ctggggttgc t                                         21

<210> SEQ ID NO 12
<211> LENGTH: 30
<212> TYPE: DNA
<213> ORGANISM: artificial
<220> FEATURE:
<223> OTHER INFORMATION: aptamer 11F46R

<400> SEQUENCE: 12
tggggtttgg tgggtctggg gttgctggcc                                30

<210> SEQ ID NO 13
<211> LENGTH: 30
<212> TYPE: DNA
<213> ORGANISM: artificial
<220> FEATURE:
<223> OTHER INFORMATION: aptamer 11F76R

<400> SEQUENCE: 13
tggggtttgg tgggtttggg gttgctggcc                                30

<210> SEQ ID NO 14
<211> LENGTH: 30
<212> TYPE: DNA
<213> ORGANISM: artificial
<220> FEATURE:
<223> OTHER INFORMATION: aptamer 11F89R

<400> SEQUENCE: 14
tagggtttgg tgggtctggg gttgctggcc                                30

<210> SEQ ID NO 15
<211> LENGTH: 30
<212> TYPE: DNA
<213> ORGANISM: artificial
<220> FEATURE:
<223> OTHER INFORMATION: aptamer 11F57R

<400> SEQUENCE: 15
ccggggtttg gtgggtctgg ggtagttggc                                30

<210> SEQ ID NO 16
<211> LENGTH: 30
<212> TYPE: DNA
<213> ORGANISM: artificial
<220> FEATURE:
<223> OTHER INFORMATION: aptamer 8F68R

<400> SEQUENCE: 16
ttggggtttg gtgggtctgg ggttgcgggt                                30

<210> SEQ ID NO 17
<211> LENGTH: 30
<212> TYPE: DNA
<213> ORGANISM: artificial
<220> FEATURE:
<223> OTHER INFORMATION: aptamer 8F44R

<400> SEQUENCE: 17
```
gcggggtttg gtgggtctgg ggttgttggt                                        30

<210> SEQ ID NO 18
<211> LENGTH: 25
<212> TYPE: DNA
<213> ORGANISM: artificial
<220> FEATURE:
<223> OTHER INFORMATION: aptamer 8F14min

<400> SEQUENCE: 18
tatggcacgg ggttggtgtt gggtt                                             25

<210> SEQ ID NO 19
<211> LENGTH: 30
<212> TYPE: DNA
<213> ORGANISM: artificial
<220> FEATURE:
<223> OTHER INFORMATION: aptamer 8F14R

<400> SEQUENCE: 19
tcgtatggca cggggttggt gttgggttgg                                        30

<210> SEQ ID NO 20
<211> LENGTH: 30
<212> TYPE: DNA
<213> ORGANISM: artificial
<220> FEATURE:
<223> OTHER INFORMATION: aptamer 8F19R

<400> SEQUENCE: 20
ctggcgcggg gttggtgtcg ggtttggttt                                        30

<210> SEQ ID NO 21
<211> LENGTH: 27
<212> TYPE: DNA
<213> ORGANISM: artificial
<220> FEATURE:
<223> OTHER INFORMATION: aptamer 8F27min

<400> SEQUENCE: 21
cgagggtttg gcttacggcg cctggcg                                           27

<210> SEQ ID NO 22
<211> LENGTH: 30
<212> TYPE: DNA
<213> ORGANISM: artificial
<220> FEATURE:
<223> OTHER INFORMATION: aptamer 8F27R

<400> SEQUENCE: 22
ccgcgagggt ttggcttacg gcgcctggcg                                        30

<210> SEQ ID NO 23
<211> LENGTH: 30
<212> TYPE: DNA
<213> ORGANISM: artificial
<220> FEATURE:
<223> OTHER INFORMATION: aptamer 8F50R

<400> SEQUENCE: 23
ccgttgggat tggcttcggt gcctggcgtg                                        30

<210> SEQ ID NO 24
<211> LENGTH: 29
<212> TYPE: DNA

```
<213> ORGANISM: artificial
<220> FEATURE:
<223> OTHER INFORMATION: aptamer 8F11R

<400> SEQUENCE: 24
ggtggttggt ggggtggagg ttaggtacc                                          29

<210> SEQ ID NO 25
<211> LENGTH: 30
<212> TYPE: DNA
<213> ORGANISM: artificial
<220> FEATURE:
<223> OTHER INFORMATION: aptamer 8F70R

<400> SEQUENCE: 25
mgtagtggtt gggctgtagt ggttgggacc                                         30

<210> SEQ ID NO 26
<211> LENGTH: 27
<212> TYPE: DNA
<213> ORGANISM: artificial
<220> FEATURE:
<223> OTHER INFORMATION: aptamer 8F77min

<400> SEQUENCE: 26
gtggttgggg tatggttggt acaggtt                                            27

<210> SEQ ID NO 27
<211> LENGTH: 30
<212> TYPE: DNA
<213> ORGANISM: artificial
<220> FEATURE:
<223> OTHER INFORMATION: aptamer 8F77R

<400> SEQUENCE: 27
gaagtggttg gggtatggtt ggtacaggtt                                         30

<210> SEQ ID NO 28
<211> LENGTH: 30
<212> TYPE: DNA
<213> ORGANISM: artificial
<220> FEATURE:
<223> OTHER INFORMATION: aptamer 8F21R

<400> SEQUENCE: 28
tggctggyga ccttgcgggt ggggggggtgg                                        30

<210> SEQ ID NO 29
<211> LENGTH: 30
<212> TYPE: DNA
<213> ORGANISM: artificial
<220> FEATURE:
<223> OTHER INFORMATION: aptamer 8F67R

<400> SEQUENCE: 29
cctgcgccgt gattaggggt ggggggggtgg                                        30

<210> SEQ ID NO 30
<211> LENGTH: 24
<212> TYPE: DNA
<213> ORGANISM: artificial
<220> FEATURE:
<223> OTHER INFORMATION: 5' fixed region

<400> SEQUENCE: 30
gcctgttgtg agcctcctgt cgaa                                               24
```

<210> SEQ ID NO 31
<211> LENGTH: 23
<212> TYPE: DNA
<213> ORGANISM: artificial
<220> FEATURE:
<223> OTHER INFORMATION: 3' fixed region

<400> SEQUENCE: 31
ttgagcgttt attcttgtct ccc                                    23

<210> SEQ ID NO 32
<211> LENGTH: 41
<212> TYPE: DNA
<213> ORGANISM: artificial
<220> FEATURE:
<223> OTHER INFORMATION: aptamer 11F46A

<400> SEQUENCE: 32
tcgaatgggg tttggtgggt ctggggttgc tggccttgag c                 41

<210> SEQ ID NO 33
<211> LENGTH: 31
<212> TYPE: DNA
<213> ORGANISM: artificial
<220> FEATURE:
<223> OTHER INFORMATION: aptamer 11F46B

<400> SEQUENCE: 33
tcgaatgggg tttggtgggt ctggggttgc t                            31

<210> SEQ ID NO 34
<211> LENGTH: 31
<212> TYPE: DNA
<213> ORGANISM: artificial
<220> FEATURE:
<223> OTHER INFORMATION: aptamer 11F46C

<400> SEQUENCE: 34
tttggtgggt ctggggttgc tggccttgag c                            31

<210> SEQ ID NO 35
<211> LENGTH: 41
<212> TYPE: DNA
<213> ORGANISM: artificial
<220> FEATURE:
<223> OTHER INFORMATION: aptamer 8F14A

<400> SEQUENCE: 35
tcgaatcgta tggcacgggg ttggtgttgg gttggttgag c                 41

<210> SEQ ID NO 36
<211> LENGTH: 33
<212> TYPE: DNA
<213> ORGANISM: artificial
<220> FEATURE:
<223> OTHER INFORMATION: aptamer 8F14B

<400> SEQUENCE: 36
tcgaatcgta tggcacgggg ttggtgttgg gtt                          33

<210> SEQ ID NO 37
<211> LENGTH: 33
<212> TYPE: DNA
<213> ORGANISM: artificial
<220> FEATURE:

```
<223> OTHER INFORMATION: aptamer 8F14C

<400> SEQUENCE: 37
tatggcacgg ggttggtgtt gggttggttg agc                                   33

<210> SEQ ID NO 38
<211> LENGTH: 41
<212> TYPE: DNA
<213> ORGANISM: artificial
<220> FEATURE:
<223> OTHER INFORMATION: aptamer 8F27A

<400> SEQUENCE: 38
tcgaaccgcg agggtttggc ttacggcgcc tggcgttgag c                          41

<210> SEQ ID NO 39
<211> LENGTH: 28
<212> TYPE: DNA
<213> ORGANISM: artificial
<220> FEATURE:
<223> OTHER INFORMATION: aptamer 8F27B

<400> SEQUENCE: 39
cgagggtttg gcttacggcg cctggcgt                                         28

<210> SEQ ID NO 40
<211> LENGTH: 77
<212> TYPE: DNA
<213> ORGANISM: artificial
<220> FEATURE:
<223> OTHER INFORMATION: aptamer 11F46

<400> SEQUENCE: 40
gcctgttgtg agcctcctgt cgaatggggt ttggtgggtc tggggttgct ggccttgagc      60
gtttattctt gtctccc                                                     77

<210> SEQ ID NO 41
<211> LENGTH: 77
<212> TYPE: DNA
<213> ORGANISM: artificial
<220> FEATURE:
<223> OTHER INFORMATION: aptamer 11F76

<400> SEQUENCE: 41
gcctgttgtg agcctcctgt cgaatggggt ttggtgggtt tggggttgct ggccttgagc      60
gtttattctt gtctccc                                                     77

<210> SEQ ID NO 42
<211> LENGTH: 77
<212> TYPE: DNA
<213> ORGANISM: artificial
<220> FEATURE:
<223> OTHER INFORMATION: aptamer 11F89

<400> SEQUENCE: 42
gcctgttgtg agcctcctgt cgaatagggt ttggtgggtc tggggttgct ggccttgagc      60
gtttattctt gtctccc                                                     77

<210> SEQ ID NO 43
<211> LENGTH: 77
<212> TYPE: DNA
<213> ORGANISM: artificial
<220> FEATURE:
<223> OTHER INFORMATION: aptamer 11F57
```

<400> SEQUENCE: 43
gcctgttgtg agcctcctgt cgaaccgggg tttggtgggt ctggggtagt tggcttgagc        60
gtttattctt gtctccc        77

<210> SEQ ID NO 44
<211> LENGTH: 77
<212> TYPE: DNA
<213> ORGANISM: artificial
<220> FEATURE:
<223> OTHER INFORMATION: aptamer 8F68

<400> SEQUENCE: 44
gcctgttgtg agcctcctgt cgaattgggg tttggtgggt ctggggttgc gggtttgagc        60
gtttattctt gtctccc        77

<210> SEQ ID NO 45
<211> LENGTH: 77
<212> TYPE: DNA
<213> ORGANISM: artificial
<220> FEATURE:
<223> OTHER INFORMATION: aptamer 8F44

<400> SEQUENCE: 45
gcctgttgtg agcctcctgt cgaagcgggg tttggtgggt ctggggttgt tggtttgagc        60
gtttattctt gtctccc        77

<210> SEQ ID NO 46
<211> LENGTH: 77
<212> TYPE: DNA
<213> ORGANISM: artificial
<220> FEATURE:
<223> OTHER INFORMATION: aptamer 8F14

<400> SEQUENCE: 46
gcctgttgtg agcctcctgt cgaatcgtat ggcacggggt tggtgttggg ttggttgagc        60
gtttattctt gtctccc        77

<210> SEQ ID NO 47
<211> LENGTH: 77
<212> TYPE: DNA
<213> ORGANISM: artificial
<220> FEATURE:
<223> OTHER INFORMATION: aptamer 8F19

<400> SEQUENCE: 47
gcctgttgtg agcctcctgt cgaactggcg cggggttggt gtcgggtttg gttttgagc        60 gtttattctt gtctccc        77

<210> SEQ ID NO 48
<211> LENGTH: 77
<212> TYPE: DNA
<213> ORGANISM: artificial
<220> FEATURE:
<223> OTHER INFORMATION: aptamer 8F27

<400> SEQUENCE: 48
gcctgttgtg agcctcctgt cgaaccgcga gggtttggct tacggcgcct ggcgttgagc        60
gtttattctt gtctccc        77

<210> SEQ ID NO 49

<211> LENGTH: 77
<212> TYPE: DNA
<213> ORGANISM: artificial
<220> FEATURE:
<223> OTHER INFORMATION: aptamer 8F50

<400> SEQUENCE: 49
gcctgttgtg agcctcctgt cgaaccgttg ggattggctt cggtgcctgg cgtgttgagc    60
gtttattctt gtctccc                                                  77

<210> SEQ ID NO 50
<211> LENGTH: 77
<212> TYPE: DNA
<213> ORGANISM: artificial
<220> FEATURE:
<223> OTHER INFORMATION: aptamer 8F11

<400> SEQUENCE: 50
gcctgttgtg agcctcctgt cgaatggtgg ttggtgggggt ggaggttagg taccttgagc   60
gtttattctt gtctccc                                                  77

<210> SEQ ID NO 51
<211> LENGTH: 77
<212> TYPE: DNA
<213> ORGANISM: artificial
<220> FEATURE:
<223> OTHER INFORMATION: aptamer 8F70

<400> SEQUENCE: 51
gcctgttgtg agcctcctgt cgaamgtagt ggttgggctg tagtggttgg gaccttgagc    60
gtttattctt gtctccc                                                  77

<210> SEQ ID NO 52
<211> LENGTH: 77
<212> TYPE: DNA
<213> ORGANISM: artificial
<220> FEATURE:
<223> OTHER INFORMATION: aptamer 8F77

<400> SEQUENCE: 52
gcctgttgtg agcctcctgt cgaagaagtg gttggggtat ggttggtaca ggttttgagc    60
gtttattctt gtctccc                                                  77

<210> SEQ ID NO 53
<211> LENGTH: 77
<212> TYPE: DNA
<213> ORGANISM: artificial
<220> FEATURE:
<223> OTHER INFORMATION: aptamer 8F21

<400> SEQUENCE: 53
gcctgttgtg agcctcctgt cgaatggctg gygaccttgc gggtgggggg gtggttgagc    60
gtttattctt gtctccc                                                  77

<210> SEQ ID NO 54
<211> LENGTH: 77
<212> TYPE: DNA
<213> ORGANISM: artificial
<220> FEATURE:
<223> OTHER INFORMATION: aptamer 8F67

-continued

```
<400> SEQUENCE: 54
gcctgttgtg agcctcctgt cgaacctgcg ccgtgattag gggtgggggg gtggttgagc    60
gtttattctt gtctccc                                                  77

<210> SEQ ID NO 55
<211> LENGTH: 77
<212> TYPE: DNA
<213> ORGANISM: artificial
<220> FEATURE:
<223> OTHER INFORMATION: aptamer 8F5

<400> SEQUENCE: 55
gcctgttgtg agcctcctgt cgaattggtg ggatgggggg ggggttgttc ggctttgagc    60
gtttattctt gtctccc                                                  77

<210> SEQ ID NO 56
<211> LENGTH: 77
<212> TYPE: DNA
<213> ORGANISM: artificial
<220> FEATURE:
<223> OTHER INFORMATION: aptamer 8F9

<400> SEQUENCE: 56
gcctgttgtg agcctcctgt cgaactgggg gtgtgtygcg attgtgtggg tgggttgagc    60
gtttattctt gtctccc                                                  77

<210> SEQ ID NO 57
<211> LENGTH: 77
<212> TYPE: DNA
<213> ORGANISM: artificial
<220> FEATURE:
<223> OTHER INFORMATION: aptamer 8F60

<400> SEQUENCE: 57
gcctgttgtg agcctcctgt cgaascscgg tggaytggtt gggtttggat cccctttgagc   60 gtttattctt gtctccc                                                  77

<210> SEQ ID NO 58
<211> LENGTH: 77
<212> TYPE: DNA
<213> ORGANISM: artificial
<220> FEATURE:
<223> OTHER INFORMATION: aptamer 8F65

<400> SEQUENCE: 58
gcctgttgtg agcctcctgt cgaatgaggg gggtggatgg gagggttccg cacgttgagc    60
gtttattctt gtctccc                                                  77

<210> SEQ ID NO 59
<211> LENGTH: 77
<212> TYPE: DNA
<213> ORGANISM: artificial
<220> FEATURE:
<223> OTHER INFORMATION: aptamer 11F2

<400> SEQUENCE: 59
gcctgttgtg agcctcctgt cgaatggacg gtgggttggg gcgggggtg tccattgagc     60 gtttattctt gtctccc                                                  77
```

```
<210> SEQ ID NO 60
<211> LENGTH: 23
<212> TYPE: DNA
<213> ORGANISM: artificial
<220> FEATURE:
<223> OTHER INFORMATION: P3 primer

<400> SEQUENCE: 60
gggagacaag aataaacgct caa                                              23

<210> SEQ ID NO 61
<211> LENGTH: 44
<212> TYPE: DNA
<213> ORGANISM: artificial
<220> FEATURE:
<223> OTHER INFORMATION: P5 primer

<400> SEQUENCE: 61
actgactgac tgactgacta cgggagacaa gaataaacgc tcaa                       44
```

APTAMERS INHIBITING THE ENZYMATIC ACTIVITY OF THE MMP-9 PROTEIN

CROSS-REFERENCE TO RELATED APPLICATIONS

This application is a U.S. National Stage Application pursuant to 35 U.S.C. § 371 of International Patent Application PCT/EP2014/079471, filed on Dec. 30, 2014, and published as WO 2015/101637 on Jul. 9, 2015, which claims priority to French Patent Application 1363696, filed on Dec. 30, 2013, all of which are incorporated herein by reference in their entireties for all purposes.

The present invention relates to a novel highly-specific matrix metalloproteinase inhibitor and to the use thereof in cosmetic or pharmaceutical compositions, in particular as active agent for combatting extrinsic and/or intrinsic skin aging and/or adipose tissue development, by inhibiting degradation of epidermal and/or dermal and/or hypodermal extracellular matrices.

External aggressions such as UV rays; sunlight; thermal, oxidative and hydric stresses; and xenobiotic agents are factors involved in skin remodeling and the skin aging process, in particular by triggering inflammatory reactions via cytokine release inducing the production of matrix metalloproteinases (MMPs).

MMPs are proteases associated with the degradation and reconstitution of extracellular matrix proteins. At least 11 types of human MMPs are known. These include collagenases (MMP-1, MMP-8 and MMP-13) and gelatinases (MMP-2 and MMP-9). MMPs differ in terms of substrate and site of expression.

The gelatinases MMP-2 and MMP-9 are known to break down basement membrane components such as collagen IV, collagen V, laminin and elastin, which play an important role in maintaining skin structure. Production of these metalloproteinases, caused by cytokines such as TGF-β, results in the reduction and degeneration of extracellular matrices, phenomena considered an important factor in changes in the physical characteristics of the skin (Inomata et al., 2003, 120). Accumulation of this damage is one of the leading causes of wrinkle formation, loss of skin texture, and reduced skin elasticity.

In order to prevent the appearance of signs, visible or not, of skin aging, and to attenuate the evolution thereof, it is thus important to control the activity of these metalloproteinases in the skin.

Keratinocytes, which make up the epidermis exposed to UVs and other external triggers of inflammation, express MMP-9. Thus, it was envisaged to develop specific MMP-9 inhibitors.

MMP inhibitors are known, although they have disadvantages which limit their benefit and use on the skin.

Certain chelating agents such as EDTA and o-phenanthroline inhibit the active metal center of MMPs, but have low specificity and are cytotoxic. Such agents cannot therefore be applied directly to the skin.

Other low molecular weight inhibitors such as peptides have been used. However, they showed that their use in cosmetic products can cause side effects in the skin (Bertin et al., 2005).

Retinoic acid has also been used as MMP-9 inhibitor (Lateef et al., 2004), but this compound has many undesirable effects.

Faced with the disadvantages following from the use of these inhibitors, it is particularly beneficial for the cosmetics industry to have at hand cosmetic agents that can be used in the field of antiaging and that are both effective on the target concerned and also sufficiently specific to limit undesirable effects when used in compositions to be applied to the skin.

This is all the more important as weakened skin, such as aged skin, proves to be particularly sensitive and likely to react negatively to the application of said compositions.

The aim of the present invention is to solve the above-mentioned problems and disadvantages of the techniques of the prior art and to propose a particularly advantageous solution for regulating the degradation of extracellular matrix components, so as to control skin remodeling effectively, to prevent or attenuate aging-related changes in skin appearance and properties, in particular those related to external aggressions.

SUMMARY OF THE INVENTION

The invention has as an object a metalloproteinase-9 (MMP-9) inhibitor, used topically to regulate the degradation of extracellular matrix components and thus to control skin remodeling and/or to prevent the appearance of signs of skin aging or to attenuate the evolution thereof.

Surprisingly, the present Inventors observed that a DNA aptamer capable of specifically binding to MMP-9 protein and inhibiting all enzymatic activity of said protein met all these criteria. In particular, this aptamer, which has a G-quadruplex structure, is able to penetrate skin cells.

To select and isolate MMP-9-inhibiting aptamers, the Inventors used a library of phosphotriester oligonucleotide sequences (same composition as natural DNA). The selection was carried out in a directed manner to identify, isolate and characterize sequences that can specifically interact with metalloproteinase-9 and inhibit the enzymatic activity thereof on extracellular matrix.

These aptamers were then tested for their ability to inhibit the enzymatic activity of MMP-9, on synthetic substrate, on cells, and on a skin model.

A first object of the invention thus relates to a G-quadruplex-structured aptamer capable of inhibiting the enzymatic activity of MMP-9 protein.

A second object of the invention relates to the use of an aptamer according to the invention to inhibit the enzymatic activity of MMP-9 protein.

A third object of the invention relates to a cosmetic or pharmaceutical composition comprising as active agent an aptamer according to the invention in an amount sufficient to inhibit the enzymatic activity of MMP-9 protein and one or more cosmetically or pharmaceutically acceptable excipients.

A fourth object of the invention relates to the cosmetic use of an aptamer according to the invention.

A fifth object of the invention relates to an aptamer according to the invention as medicinal product.

A sixth object of the invention relates to an aptamer according to the invention for use in treating and/or preventing pathologies associated with MMP-9 overexpression or hyperactivity.

A seventh object of the invention relates to a method for selecting an aptamer according to the invention comprising the following steps:

selecting in an oligonucleotide library, using the SELEX method, aptamers against the catalytic site of MMP-9 protein, evaluating the potential to inhibit the enzymatic activity of MMP-9 protein of the aptamers selected in the preceding step, cloning and sequencing the aptamers thus selected.

SUMMARY OF THE FIGURES

FIG. 1: Sequences of DNA aptamers selected against the catalytic domain of MMP-9 The most-represented aptamer sequences were grouped according to a consensus motif contained in the random regions, represented by the nucleotides enclosed in boxes. The common regions (i.e., constant regions) corresponding to the primers are not represented. The groups of sequences and candidates (i.e., aptamer reference) obtained in rounds 8 and 11 are indicated on the left, while the number of sequences belonging to the same group is indicated on the right. The nucleotides indicated in gray are likely to contribute to G-quartets. From top to bottom: SEQ ID NO: 12; SEQ ID NO: 22; SEQ ID NO: 19; SEQ ID NO: 24; SEQ ID NO: 28; SEQ ID NO: 6; SEQ ID NO: 7; SEQ ID NO: 8; SEQ ID NO: 9; SEQ ID NO: 10.

FIG. 2: Sequences of shortened DNA aptamers.

The names of the sequences are indicated on the left. The sequences were truncated in order to define the minimal region necessary to interaction with the catalytic domain of MMP-9 protein. From top to bottom: SEQ ID NO: 12; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39.

Figure 3:
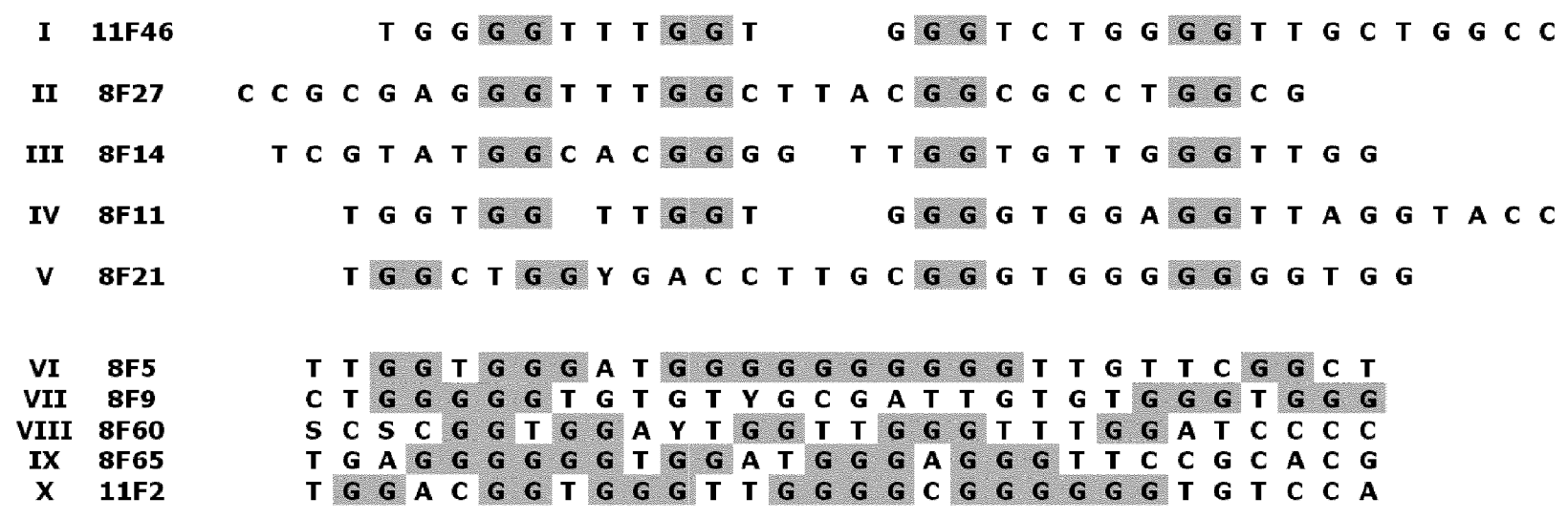

FIG. 3: Sequence homology analysis-G-quartets

G-doublets of the sequences 11F46, 8F27, 8F14, 8F11 and 8F21 capable of being involved in G-quartet formation are indicated in gray. Circular dichroism and Tm experiments confirmed that the sequences 11F46, 8F27 and 8F14 are G-quartet-structured. From top to bottom: SEQ ID NO: 12; SEQ ID NO: 22; SEQ ID NO: 19; SEQ ID NO: 24; SEQ ID NO: 28; SEQ ID NO: 6; SEQ ID NO: 7; SEQ ID NO: 8; SEQ ID NO: 9; SEQ ID NO: 10.

Figure 4:
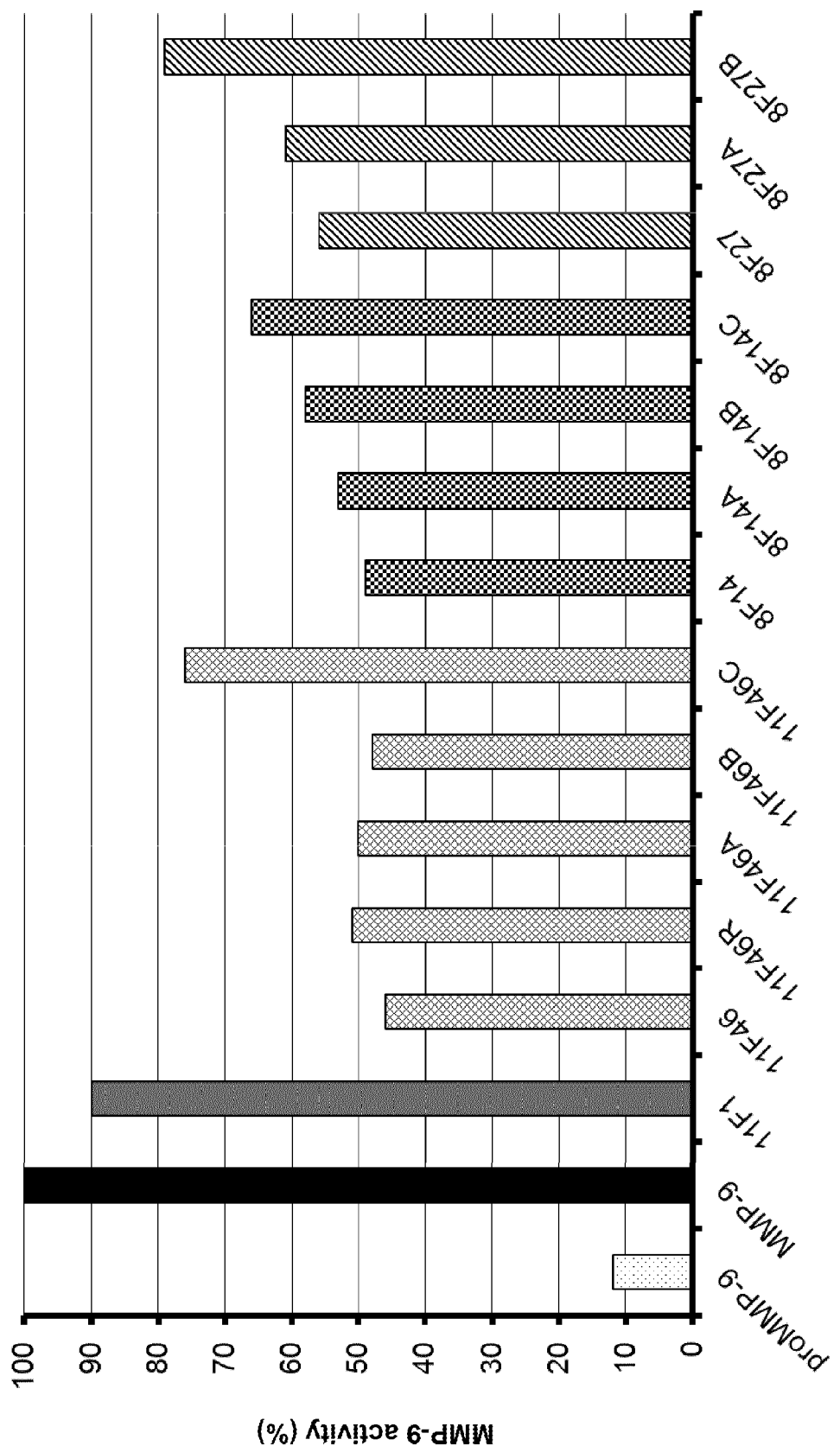

FIG. 4: MMP-9 activity

This graph represents the inhibition of the enzymatic activity of MMP-9 of the various aptamers selected in relation to the maximum activity represented by a control MMP-9(black bar).

Figure 5:
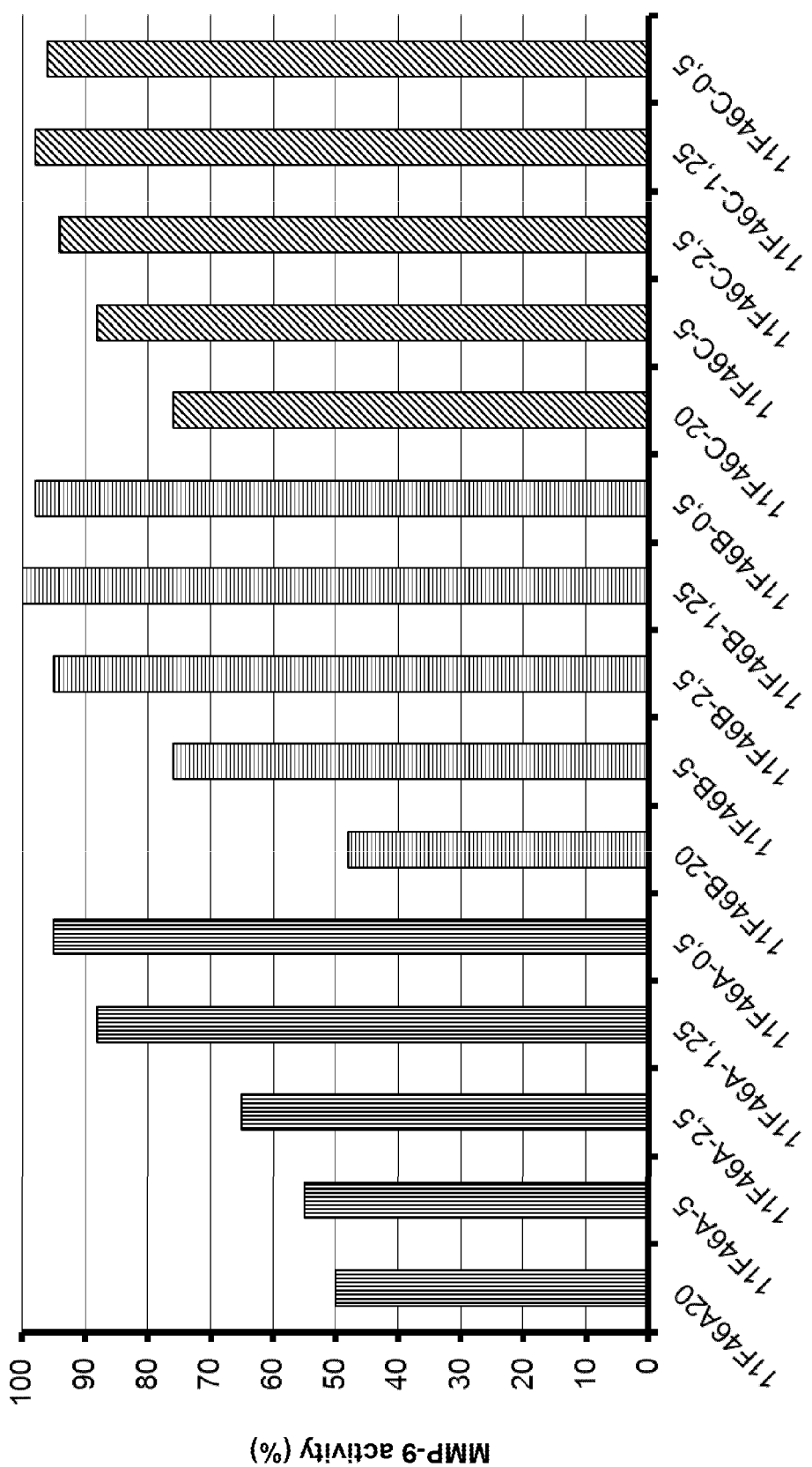
Figure 6:
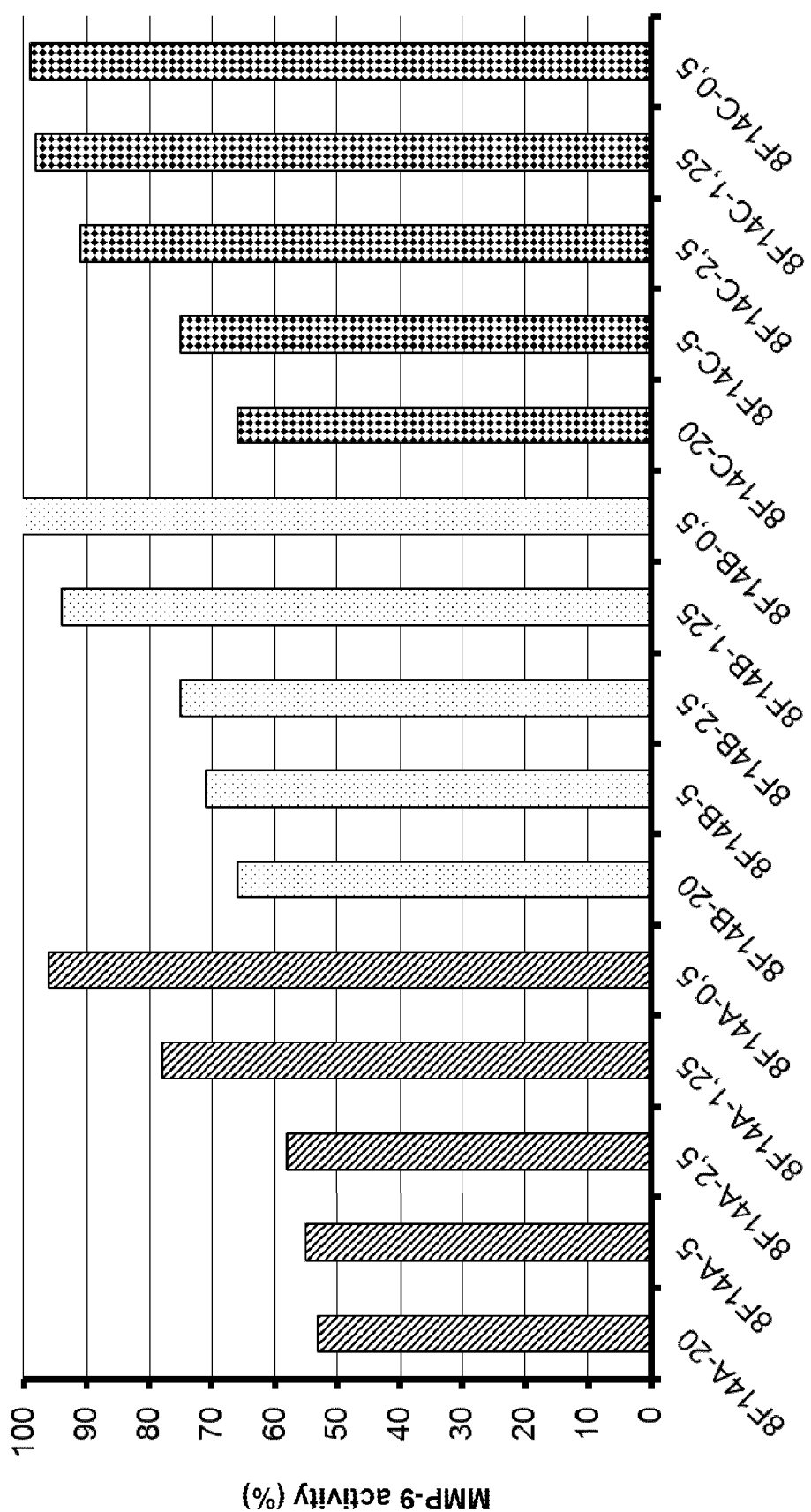

FIGS. 5 and 6: Dose-dependent effect on MMP-9 activity

These graphs represent the ability to inhibit the enzymatic activity of metalloproteinase MMP-9 of the various aptamers identified according to the dose used. The dose is indicated on the abscissa after the name of the aptamer.

DETAILED DESCRIPTION OF THE INVENTION

A first object of the present invention thus relates to a G-quadruplex-structured aptamer capable of inhibiting the enzymatic activity of metalloproteinase MMP-9.

By "aptamer" is meant a ligand-specific DNA or RNA molecule with high affinity for a protein. Consequently, this meaning comprises "natural" aptamers and chemically-modified analogs.

By "G-quadruplex-," "G-quartet-" or "G-tetrad-structured" according to the invention is meant a secondary structure comprising four guanines associated in a cyclic arrangement via Hoogsteen bonding. In this structure, each guanine is involved in four hydrogen bonds via atoms N1, N7, O6 and N2 (Williamson et al., 1989; Sundquist and Klug, 1989; Tucker et al., 2012).

By "enzymatic activity" relating to MMP-9 protein is meant proteolytic activity resulting in degradation of matrix or bioactive substrates of this protein, such as gelatin, which is a denatured form of collagen, aggrecan, entactin, elastin, collagens II, III, IV, V, XIV and XVII, myelin, endostatin, plasminogen, serine protease inhibitors, substance P, proteins CBP30 and CBP35, interleukin-2 (IL2) receptor alpha, tissue factor pathway inhibitor (TFPI), amyloid beta-peptide, pro-TNF alpha or -TGF beta, and CXC chemokines (Van den Steen et al., 2002; Folgueras et al., 2004; Chaussain-Miller et al., 2006). The enzymatic activity of MMP-9 protein according to the present invention is preferably gelatinase activity. In the context of the present invention, the measurement of MMP-9 proteolytic activity can be confirmed according to the method described below in Example 3: measurement of the enzymatic activity of MMPs is based on the principle of resonance energy transfer, RET, or fluorescence resonance energy transfer, FRET. The substrate consists of an oligopeptide comprising a fluorescent group (F), energy donor, and a quenching group (Q), energy acceptor. After hydrolysis, the quenching group is released, making it possible to measure the increase in fluorescence. Many fluorophore/quencher pairs have been developed for measuring the enzymatic activity of MMPs, including the pair 7-methoxycoumarin-4-acetyl (Mca)/dinitrophenyl-diaminopropionyl (Dnp) (Knight et al., 1991; Knight et al., 1992).

Aptamers are selected by the alternation of selection and amplification, which makes it possible to direct the evolution of the population in a Darwinian manner: in the population, the most "apt" molecules are selected, hence the origin of the name "aptamers" given to oligonucleotides having the desired feature, arising from the selection. Standard genetic engineering techniques (cloning, sequencing, expression) can be used to identify these aptamers individually, to characterize them and then to produce them in large amounts.

Aptamer selection can be carried out by means of an optimized in vitro selection protocol known as systemic evolution of ligands by exponential enrichment (SELEX), described in particular in international application WO 91/19813.

The SELEX process makes it possible to generate in large amounts ligands with very high affinity and specificity. This approach is based on the exposure of the target molecule to a library of potential ligands. A system of desorption/selection cycles makes it possible to enrich the population of ligands interacting most specifically with the target molecule. The final population obtained is then isolated and characterized, allowing its large-scale resynthesis.

Although the SELEX process has been established as a general technique for selecting aptamers, it is nevertheless neither predictive nor standardized for any target. On the contrary, the SELEX process must be optimized and adapted for each particular target. The SELEX process is not guaranteed for every target.

Several factors are important when selecting aptamers. For example, the target molecule must be stable and easily reproducible in each SELEX cycle, because the SELEX process involves several cycles of binding, selection and amplification. In addition, nucleic acids that exhibit specific binding to the target must be present in the initial library. Thus, it is necessary to produce a highly-diversified initial nucleic acid library.

Considering these critical factors, selecting aptamers by means of the SELEX process is neither predictive nor obvious. Even if all the factors are optimum for selecting aptamers, the SELEX process does not always make it possible to obtain viable aptamers for each target.

The initial candidate library is made up of chemically synthesized oligonucleotide sequences, each comprising a long variable region of n nucleotides flanked, at the 3' and 5' ends, by identical constant regions for all the candidates of the library. These constant regions allow the central portion to be manipulated during SELEX, in particular by means of PCR. The length of the variable portion determines the library's diversity, which is equal to $4^n$ since each position can be occupied by one of four nucleotides A, T (or U), G or C. For large windows, huge complexities arise: when n=50 theoretical diversity is $4^{50}$ ($10^{30}$), which is in practice an inaccessible value as it corresponds to more than $10^5$ tons for a library wherein each sequence is represented once. The experimental limit is around $10^{15}$ different sequences, which is that of a library wherein all candidates having a 25-nucleotide variable region are represented. If one chooses to manipulate a library comprising a 30-nucleotide window whose theoretical diversity is about $10^{18}$, only 1/1000 of the possibilities will thus be explored.

In addition, since the polymerases used are unreliable and introduce errors at a rate on the order of $10^{-4}$, they contribute to significantly enrich the diversity of the sequence pool throughout the SELEX process: one candidate in 100 will be modified in each amplification cycle for a library with a random region of 100 nucleotides in length, thus leading to the appearance of $10^{13}$ new candidates for the overall library.

Selection in each round occurs by means of physical separation of molecules associated with the target from free molecules. Multiple techniques may be applied (chromatography, filter retention, electrophoresis, etc.). The selection conditions are adjusted (relative concentration of target/candidates, ion concentration, temperature, washing, etc.) so that a target-binding competition occurs between the candidates. Generally, stringency is increased as the rounds proceed in order to promote the capture of candidates with the highest affinity. In addition, counter-selection is carried out to eliminate candidates that recognize the support (filter, beads, etc.).

Oligonucleotides are oligo-anions, each unit having a charge at neutral pH, hydrogen-bond donor/acceptor sites, and an aromatic heterocycle (the nucleic base) that can generate stacking interactions. Following the formation of base pairs, these oligomers fold to generate secondary and tertiary structures such as stem-loop (or hairpin), pseudoknot or G-quadruplex structures. The initial sequence library is thus a library of three-dimensional shapes, each corresponding to a distribution of units that can trigger electrostatic interactions, create H bonds, etc. Selection becomes a question of identifying in the library the shape suited to the target, i.e., the shape allowing the greatest number of interactions and the formation of the most stable aptamer-target complex. For small targets (dyes, antibiotics, etc.), the aptamers identified are characterized by equilibrium dissociation constants in the micromolar range, whereas for protein targets $K_d$ values below $10^{-9}$ M are not rare.

The most remarkable property of aptamers is the specificity of the interactions engaged with their ligand, making them ideal agents for target recognition.

Thus, preferably, the aptamer according to the invention binds specifically to MMP-9 protein. By "specific binding" is a specific interaction of the aptamer with its target, excluding any interaction with a foreign target having a different structure.

More preferably, said aptamer binds specifically with high affinity to said MMP-9 protein. By "specific binding with high affinity" is meant, within the meaning of the present invention, a specific interaction of the aptamer with its target, with a dissociation constant ($K_d$) sufficiently low to allow significant inhibition of the catalytic activity of the targeted enzyme.

In the context of the present invention, the catalytic site isolated from MMP-9 protein was used to generate the aptamer according to the invention. The person skilled in the art is capable of isolating and expressing said catalytic site using molecular biology techniques well established in the art. Preferably, the peptide fragment Phe88-Pro438 of human MMP-9 protein, which contains the catalytic site of this enzyme, was used to generate the aptamer according to the invention (accession number of human MMP-9 protein: P14780 according to the UniProtKB/Swiss-Prot database).

Aptamers can be oligodeoxynucleotides (DNA) or oligoribonucleotides (RNA). In the latter case, the first SELEX step can consist in transcribing the initial DNA library via the promoter sequence of the candidates' 5' constant region. After selection, the candidates are converted into DNA by reverse transcription before being amplified. RNA and DNA aptamers having comparable characteristics were selected against the same target. Additionally, both compounds are competitive inhibitors of one another, suggesting overlapping interaction sites. That has major consequences for the production of chemically modified aptamers.

Development of the antisense approach led to synthesis of a large number of analogs, including some, for example, which give the oligomer resistance to nucleases, a property useful in a biological environment (cell culture medium or in vivo). Modifications of the phosphodiester bond, sugar or sugar-phosphate backbone, such as 2'-O-methyl, "locked" nucleic acid or boranophosphate derivatives, lead to nuclease-resistant oligomers. This property may be advantageous for aptamers. However, as mentioned above, the subsequent complete change of chemical structure of an aptamer selected in RNA or DNA form generally leads to a decrease in or a loss of the properties for which it was selected. That does not mean that it is not possible to introduce modifications at certain positions. But it is advisable to identify the positions at which modifications are tolerated. That can be carried out by testing specific variants or by a systematic approach, so-called chemical interference, which is a variant of footprinting.

Preferably, the aptamer according to the invention is a DNA aptamer.

In the context of the invention, it is preferable to perform the selection of non-natural oligonucleotides directly. That assumes that the modified nucleoside triphosphates are efficiently incorporated and the modified matrices are read correctly by the polymerases used during SELEX. A very small number of analogs meet the requirements. As for derivatives conferring resistance to nucleases, the possibilities are limited to phosphorothioate, boranophosphate or 2'-methyl-, 2'-amino- or 2'-fluoro-pyrimidine analogs, the latter being by far the most commonly used. The aptamers identified in this case have modified pyrimidine nucleosides and unmodified purine residues (2'-hydroxyl). These molecules have greater resistance to nucleases. If necessary, modified purine residues can be introduced later, as indicated above. Furthermore, it is possible to select oligonucleotides comprising substituents at the C(5) position of pyrimidines or the N(7), C(8) position of purines. That has no effect on sensitivity to nucleases, but makes it possible to add new functionalities (hydrophobicity, photoreactivity, etc.). A very different approach relates to the use of optical isomers. Natural nucleic acids are D-isomers. L-analogs are resistant to nucleases but cannot be produced by polymerases. According to the laws of optical isomerism, an L-series aptamer will form with its target (T) a complex having the same characteristics as the complex formed by the D-series isomer and the enantiomer (T') of the target (T). Consequently, if compound T' can be chemically synthesized, it will be used to perform the selection of a natural aptamer (D). Once identified, this aptamer will be chemically synthesized in an L-series. This L-aptamer will be a ligand of the natural target (T).

Another approach, recently described as two-dimensional SELEX, simultaneously applies in vitro oligonucleotide selection and dynamic combinatorial chemistry (DCC), i.e., a reversible reaction between certain groups of the oligonucleotide (amine groups) and a library of aldehyde compounds. The reaction produces imine oligonucleotides which are selected on the same principles as for conventional SELEX. It was thus possible to identify for a target hairpin RNA modified aptamers that differ from natural aptamers.

Unlike backbone modifications which can alter the structure and which require precautions to be taken before being introduced in order to avoid losing aptamer-target interaction properties, it is possible to conjugate various groups at one of the 3' or 5' ends of the oligonucleotide in order to convert it into a tool, probe or sensor without disrupting its characteristics. This versatility constitutes in addition a significant advantage of aptamers, in particular in terms of diagnostics.

The expression "aptamer analog" means herein one or more modifications described above.

According to a preferred embodiment of the invention, the aptamer is resistant to nucleases.

Preferably, the aptamer according to the invention comprises at least one modification of the phosphodiester bond, sugar or sugar-phosphate backbone selected form the group of 2'-alkyl, 2'-amino and 2'-fluoro derivatives on the sugar, phosphorothioate, methylphosphonate or boranophosphate derivatives on the backbone, or locked nucleic acids (LNA) or peptide nucleic acids (PNA).

According to a preferred embodiment of the invention, the aptamer comprises a nucleotide sequence selected from the group consisting of the sequences SEQ ID NO: 1 to SEQ ID NO: 10, as defined below:

```
                                              (SEQ ID NO: 1)
5'X1X2X3X4TTTGGTGGGTYTGGGGTWGYKX5X63',
where X represents 0 or 1 G nucleotide;

(SEQ ID NO: 2)
5'TGGCRCGGGGTTGGTGTYGGGTT3';

(SEQ ID NO: 3)
5'GGGWTTGGCTTX7CGGYGCCTGGCG3',
where X represents 0 or 1 A nucleotide;

(SEQ ID NO: 4)
5'GTGGTTGGX8GSKRTRGWKGKT3',
where X represents 0 or 1 T nucleotide;

(SEQ ID NO: 5)
5'GGGTGGGGGGTGG3';

(SEQ ID NO: 6)
5'TTGGTGGGATGGGGGGGGGTTGTTCGGCT3';

(SEQ ID NO: 7)
5'CTGGGGGTGTGTYGCGATTGTGTGGGTGGG3';
```

```
                                              (SEQ ID NO: 8)
5'SCSCGGTGGAYTGGTTGGGTTTGGATCCCC3';

(SEQ ID NO: 9)
5'TGAGGGGGGTGGATGGGAGGGTTCCGCACG3';
and (SEQ ID NO: 10)
5'TGGACGGTGGGTTGGGGCGGGGGGTGTCCA3'.
```

Said sequences are consensus sequences in accordance with the IUPAC nomenclature commonly used to designate nucleotides (Table 1).

TABLE 1

| one-letter nucleotide code | corresponding nucleotides |
|---|---|
| A | adenine |
| G | guanine |
| C | cytosine |
| T | thymine |
| U | uracil |
| R | adenine or guanine (purines) |
| Y | cytosine or thymine (pyrimidine) |
| N | any nucleotide |
| W | adenine or thymine (weak) |
| S | guanine or cytosine (strong) |
| M | adenine or cytosine (amino) |
| K | guanine or thymine (keto) |
| B | not adenine (guanine, cytosine or thymine) |
| H | not guanine (adenine, cytosine or thymine) |
| D | not cytosine (adenine, guanine or thymine) |
| V | not thymine (adenine, guanine or cytosine) |

Preferably, the aptamer according to the invention comprises a nucleotide sequence selected from the group consisting of the sequences SEQ ID NO: 6 to SEQ ID NO: 29.

More preferably, said nucleotide sequence comprises at least 1 to 24 contiguous nucleotides of the sequence SEQ ID NO: 30 flanked at its 5' end, and/or at least 1 to 23 contiguous nucleotides of the sequence SEQ ID NO: 31 flanked at its 3' end.

More preferably, said nucleotide sequence is selected from the group consisting of the sequences:

SEQ ID NO: 6 to SEQ ID NO: 10, SEQ ID NO: 12 to SEQ ID NO: 17, SEQ ID NO: 19 to SEQ ID NO: 20, SEQ ID NO: 22 to SEQ ID NO: 25, and SEQ ID NO: 27 to SEQ ID NO: 29, and comprises at least 1 to 24 contiguous nucleotides of the sequence SEQ ID NO: 30 flanked at its 5' end, and/or at least 1 to 23 contiguous nucleotides of the sequence SEQ ID NO: 31 flanked at its 3' end.

Mention can thus be made, for example, of the sequences SEQ ID NO: 32 to SEQ ID NO: 39, and preferably the sequences SEQ ID NO: 40 to SEQ ID NO: 59.

The particularly preferred sequences according to the invention are selected from the sequences SEQ ID NO: 12, SEQ ID NO: 32 to SEQ ID NO: 40, SEQ ID NO: 46, and SEQ ID NO: 48.

Table 2 below summarizes these sequences, which were grouped into 10 main groups of highly homologous sequences (i.e., groups I to X). The person skilled in the art will easily understand from Table 2 below that:

the sequences SEQ ID NO: 11 to 17, 32 to 34 and 40 to 45 are included in the consensus sequence SEQ ID NO: 1 (group I);

the sequences SEQ ID NO: 18 to 20, 35 to 37 and 46 and 47 are included in the consensus sequence SEQ ID NO: 2 (group II);

the sequences SEQ ID NO: 21 to 23, 38, 39, 48 and 49 are included in the consensus sequence SEQ ID NO: 3 (group III);
the sequences SEQ ID NO: 24 to 27 and 50 to 52 are included in the consensus sequence SEQ ID NO: 4 (group IV);
the sequences SEQ ID NO: 28, 29, 53 and 54 are included in the consensus sequence SEQ ID NO: 5 (group V);
the sequence SEQ ID NO: 55 is included in the consensus sequence SEQ ID NO: 6 (group VI);

the sequence SEQ ID NO: 56 is included in the consensus sequence SEQ ID NO: 7 (group VII);
the sequence SEQ ID NO: 57 is included in the consensus sequence SEQ ID NO: 8 (group VIII);
the sequence SEQ ID NO: 58 is included in the consensus sequence SEQ ID NO: 9 (group IX); and
the sequence SEQ ID NO: 59 is included in the consensus sequence SEQ ID NO: 10 (group X).

TABLE 2

| SEQ ID NO | Nucleotide sequence (5' to 3') | Reference |
|---|---|---|
| SEQ ID NO: 30 | GCCTGTTGTGAGCCTCCTGTCGAA | 5' constant region |
| SEQ ID NO: 31 | TTGAGCGTTTATTCTTGTCTCCC | 3' constant region |
| Group I | | |
| SEQ ID NO: 1 | $X_1X_2X_3X_4$TTTGGTGGGTYTGGGGWGYKX$_5$X$_6$ | consensus I |
| SEQ ID NO: 11 | TTTGGTGGGTCTGGGGTTGCT | 11F46min |
| SEQ ID NO: 12 | TGGGGTTTGGTGGGTCTGGGGTTGCTGGCC | 11F46R |
| SEQ ID NO: 32 | TCGAATGGGGTTTGGTGGGTCTGGGGTTGCTGGCCTTGAGC | 11F46A |
| SEQ ID NO: 33 | TCGAATGGGGTTTGGTGGGTCTGGGGTTGCT | 11F46B |
| SEQ ID NO: 34 | TTTGGTGGGTCTGGGGTTGCTGGCCTTGAGC | 11F46C |
| SEQ ID NO: 40 | GCCTGTTGTGAGCCTCCTGTCGAATGGGGTTTGGTGGGTCTGGGGTTGCTGGCCTTGAGCGTTTATTCTTGTCTCCC | 11F46 |
| SEQ ID NO: 13 | TGGGGTTTGGTGGGTTTGGGGTTGCTGGCC | 11F76R |
| SEQ ID NO: 41 | GCCTGTTGTGAGCCTCCTGTCGAATGGGGTTTGGTGGGTTTGGGGTTGCTGGCCTTGAGCGTTTATTCTTGTCTCCC | 11F76 |
| SEQ ID NO: 14 | TAGGGTTTGGTGGGTCTGGGGTTGCTGGCC | 11F89R |
| SEQ ID NO: 42 | GCCTGTTGTGAGCCTCCTGTCGAATGGGGTTTGGTGGGTCTGGGGTTGCTGGCCTTGAGCGTTTATTCTTGTCTCCC | 11F89 |
| SEQ ID NO: 15 | CCGGGGTTTGGTGGGTCTGGGGTAGCTGGC | 11F57R |
| SEQ ID NO: 43 | GCCTGTTGTGAGCCTCCTGTCGAACCGGGGTTTGGTGGGTCTGGGGTAGCTGGCTTGAGCGTTTATTCTTGTCTCCC | 11F57 |
| SEQ ID NO: 16 | TTGGGGTTTGGTGGGTCTGGGGTTGCGGGT | 8F68R |
| SEQ ID NO: 44 | GCCTGTTGTGAGCCTCCTGTCGAACCGGGGTTTGGTGGGTCTGGGGTTGCGGGTTTGAGCGTTTATTCTTGTCTCCC | 8F68 |
| SEQ ID NO: 17 | GCGGGGTTTGGTGGGTCTGGGGTTGTTGGT | 8F44R |
| SEQ ID NO: 45 | GCCTGTTGTGAGCCTCCTGTCGAAGCGGGGTTTGGTGGGTCTGGGGTTGTTGGTTTGAGCGTTTATTCTTGTCTCCC | 8F44 |

********** **** * **

TABLE 2-continued

| SEQ ID NO | Nucleotide sequence (5' to 3') | Reference |
|---|---|---|
| Group II | | |
| SEQ ID NO: 2 | TGGCRCGGGGTTGGTGTYGGGTT | consensus II |
| SEQ ID NO: 18 | TATGGCACGGGGTTGGTGTTGGGTT | 8F14min |
| SEQ ID NO: 19 | TCGTATGGCACGGGGTTGGTGTTGGGTTGG | 8F14R |
| SEQ ID NO: 35 | <u>TCGAA</u>TCGTATGGCACGGGGTTGGTGTTGGGTTGG<u>TTGAGC</u> | 8F14A |
| SEQ ID NO: 36 | <u>TCGAA</u>TCGTATGGCACGGGGTTGGTGTTGGGTT | 8F14B |
| SEQ ID NO: 37 | TATGGCACGGGGTTGGTGTTGGGTTGG<u>TTGAGC</u> | 8F14C |
| SEQ ID NO: 46 | <u>GCCTGTTGTGAGCCTCCTGTCGAA</u>TCGTATGGCACGGGGTTGGTGTTGGGTTGG<u>TTGAGCGTTTATTCTTGTCTCCC</u> | 8F14 |
| SEQ ID NO: 20 | CTGGCGCGGGGTTGGTGTCGGGTTTGGTTT | 8F19R |
| SEQ ID NO: 47 | <u>GCCTGTTGTGAGCCTCCTGTCGAA</u>CTGGCGCGGGGTTGGTGTCGGGTTTGGTTT<u>TTGAGCGTTTATTCTTGTCTCCC</u> | 8F19 |
| | **** ************ ***** | |
| Group III | | |
| SEQ ID NO: 3 | GGGWTTGGCTTX$_7$CGGYGCCTGGCG | consensus III |
| SEQ ID NO: 21 | CGAGGGTTTGGCTTACGGCGCCTGGCG | 8F27min |
| SEQ ID NO: 22 | CCGCGAGGGTTTGGCTTACGGCGCCTGGCG | 8F27R |
| SEQ ID NO: 38 | <u>TCGAA</u>CCGCGAGGGTTTGGCTTACGGCGCCTGGCG<u>TTGAGC</u> | 8F27A |
| SEQ ID NO: 39 | CGAGGGTTTGGCTTACGGCGCCTGGCG<u>T</u> | 8F27B |
| SEQ ID NO: 48 | <u>GCCTGTTGTGAGCCTCCTGTCGAA</u>CCGCGAGGGTTTGGCTTACGGCGCCTGGCG<u>TTGAGCGTTTATTCTTGTCTCCC</u> | 8F27 |
| SEQ ID NO: 23 | CCGT-TGGGATTGGCTT-CGGTGCCTGGCGTG | 8F50R |
| SEQ ID NO: 49 | <u>GCCTGTTGTGAGCCTCCTGTCGAA</u>CCGT-TGGGATTGGCTT-CGGTGCCTGGCGT<u>GTTGAGCGTTTATTCTTGTCTCCC</u> | 8F50 |
| | *** *** ******* *** ******** | |
| Group IV | | |
| SEQ ID NO: 4 | GTGGTTGGX$_8$GSKRTRGWKGKT | consensus IV |
| SEQ ID NO: 24 | TGGTGGTTGGTGGGTGGAGGTTAGGTACC | 8F11R |
| SEQ ID NO: 50 | <u>GCCTGTTGTGAGCCTCCTGTCGAA</u>TGGTGGTTGGTGGGTGGAGGTTAGGTACC<u>TTGAGCGTTTATTCTTGTCTCCC</u> | 8F11 |
| SEQ ID NO: 25 | MGTAGTGGTTGG-GCTGTAGTGGTT-GGGACC | 8F70R |
| SEQ ID NO: 51 | <u>GCCTGTTGTGAGCCTCCTGTCGAA</u>MGTAGTGGTTGG-GCTGTAGTGGTT-GGGACC<u>TTGAGCGTTTATTCTTGTCTCCC</u> | 8F70 |

TABLE 2-continued

| SEQ ID NO | Nucleotide sequence (5' to 3') | Reference |
|---|---|---|
| SEQ ID NO: 26 | GTGGTTGG-GGTATGGTTGGTACAGGTT | 8F77min |
| SEQ ID NO: 27 | GAAGTGGTTGG-GGTATGGTTGGTACAGGTT | 8F77R |
| SEQ ID NO: 52 | <u>GCCTGTTGTGAGCCTCCTGTCGAA</u>GAAGTGGTTGG-GGTATGGTTGGTACAGGTT<u>TTGAGCGTTTATTCTTGTCTCCC</u> | 8F77 |
|  | ******* *   *  *  * |  |
| Group V |  |  |
| SEQ ID NO: 5 | GGGTGGGGGGGTGG | consensus V |
| SEQ ID NO: 28 | TGGCTGGYGACCTTGCGGGTGGGGGGGTGG | 8F21R |
| SEQ ID NO: 29 | CCTGCGCCGTGATTAGGGGTGGGGGGGTGG | 8F67R |
| SEQ ID NO: 53 | <u>GCCTGTTGTGAGCCTCCTGTCGAA</u>TGGCTGGYGACCTTGCGGGTGGGGGGGTGG<u>TTGAGCGTTTATTCTTGTCTCCC</u> | 8F21 |
| SEQ ID NO: 54 | <u>GCCTGTTGTGAGCCTCCTGTCGAA</u>CCTGCGCCGTGATTAGGGGTGGGGGGGTGG<u>TTGAGCGTTTATTCTTGTCTCCC</u> | 8F67 |
|  | *    **  ************* |  |
| Group VI |  |  |
| SEQ ID NO: 6 | TTGGTGGGATGGGGGGGGGTTGTTCGGCT | 8F5R |
| SEQ ID NO: 55 | <u>GCCTGTTGTGAGCCTCCTGTCGAA</u>TTGGTGGGATGGGGGGGGGTTGTTCGGCT<u>TTGAGCGTTTATTCTTGTCTCCC</u> | 8f5 |
|  | **************************** |  |
| Group VII |  |  |
| SEQ ID NO: 7 | CTGGGGGTGTGTYGCGATTGTGTGGGTGGG | 8F9R |
| SEQ ID NO: 56 | <u>GCCTGTTGTGAGCCTCCTGTCGAA</u>CTGGGGGTGTGTYGCGATTGTGTGGGTGGG<u>TTGAGCGTTTATTCTTGTCTCCC</u> | 8F9 |
|  | ****************************** |  |
| Group VIII |  |  |
| SEQ ID NO: 8 | SCSCGGTGGAYTGGTTGGGTTTGGATCCCC | 8F60R |
| SEQ ID NO: 57 | <u>GCCTGTTGTGAGCCTCCTGTCGAA</u>SCSCGGTGGAYTGGTTGGGTTTGGATCCCC<u>TTGAGCGTTTATTCTTGTCTCCC</u> | 8F60 |
|  | ****************************** |  |
| Group IX |  |  |
| SEQ ID NO: 9 | TGAGGGGGTGGATGGGAGGGTTCCGCACG | 8F65R |
| SEQ ID NO: 58 | <u>GCCTGTTGTGAGCCTCCTGTCGAA</u>TGAGGGGGTGGATGGGAGGGTTCCGCACG<u>TTGAGCGTTTATTCTTGTCTCCC</u> | 8F65 |
|  | ***************************** |  |
| Group X |  |  |
| SEQ ID NO: 10 | TGGACGGTGGGTTGGGGCGGGGGGTGTCCA | 11F2R |

TABLE 2-continued

| SEQ ID NO | Nucleotide sequence (5' to 3') | Reference |
|---|---|---|
| SEQ ID NO: 59 | GCCTGTTGTGAGCCTCCTGTCGAATGGACGGTGGGTTGGGGCGGGGGGTGTCCATTGAGCGTTTATTCTTGTCTCCC | 11F2 |

\*\*\*\*\*\*\*\*\*\*\*\*\*\*\*\*\*\*\*\*\*\*\*\*\*\*\*\*\*\*

Another object of the invention relates to the use of an aptamer according to any one of the preceding claims, to inhibit the enzymatic activity of MMP-9 protein.

Enzymatic activity can be measured according to the method described above, in particular according to the method of Example 3 below.

Another object of the invention relates to a cosmetic or pharmaceutical composition comprising as active agent at least one aptamer according to the invention in an amount sufficient to inhibit the enzymatic activity of MMP-9 protein and one or more cosmetically/pharmaceutically acceptable excipients.

Preferably, the composition of the invention comprises from 0.000001% to 10%, preferably from 0.000002% to 5%, more preferably from 0.000005% to 1% by weight of the composition of one or more aptamers according to the invention.

Generally, any composition of the invention can be applied to the skin.

It can be provided in all pharmaceutical forms normally used for topical application to the skin.

The composition of the invention can in particular have the form of aqueous or oily solutions or of lotion- or serum-type dispersions, milk-type emulsions with a liquid or semi-liquid consistency, obtained by dispersion of an aqueous phase in a silicone phase (W/Si), of a fatty phase in an aqueous phase (O/W: oil-in-water emulsion) or, conversely, of an aqueous phase in a fatty phase (W/O: water-in-oil emulsion), or aqueous or anhydrous suspensions or emulsions with a cream- or gel-type soft consistency, or of microcapsules or microparticles, or of ionic and/or nonionic-type vesicular dispersions, or of foams. These compositions are prepared using conventional methods. The amounts of the various components of the compositions according to the invention are those typically used in the fields under consideration.

In the field of cosmetics, these compositions constitute in particular creams for cleansing, protecting, treating or caring for the face, hands, feet or body (for example, day creams, night creams, makeup remover creams, foundation creams, sunscreen creams), liquid foundations, makeup remover milks, body protection or care milks, sunscreen milks, skincare lotions, gels or foams, such as cleansing lotions, sunscreen lotions, artificial tanning lotions, compositions for the bath, deodorant compositions comprising a bactericide, aftershave gels or lotions, depilatory creams.

The compositions according to the invention can also consist of powder or non-powder solid preparations, for example in the form of a stick, a compacted powder, cleansing soaps or bars. It can be provided also as patches, pencils, brushes and applicators allowing localized application on spots on the face or hands. It can be used as a care product or as a makeup product.

When the composition is an emulsion, the proportion of fatty phase may vary from about 5% to 80% by weight, and preferably from about 5% to 50% by weight in relation to the total weight of the composition. The oils, waxes, emulsifiers and co-emulsifiers used in the composition in emulsion form are selected from those typically used in the field of cosmetics. The emulsifier and co-emulsifier are present in the composition in a proportion of 0.3% to 30% by weight, and preferably of 0.5% to 20% by weight in relation to the total weight of the composition. In addition, the emulsion can contain lipid vesicles.

When the composition is an oily solution or gel, the fatty phase can represent more than 90% of the total weight of the composition.

In a known manner, the cosmetic or pharmaceutical composition of the invention can also contain adjuvants commonly used in the field of cosmetics or pharmaceuticals, such as hydrophilic or lipophilic gelling agents, hydrophilic or lipophilic active agents, preservatives, antioxidants, solvents, fragrances, fillers, filters, pigments, odor absorbers and colorants. The amounts of these various adjuvants are those typically used in the fields under consideration, and vary, for example, from about 0.01% to 10% of the total weight of the composition. These adjuvants, according to their nature, can be added to the fatty phase, to the aqueous phase and/or to lipid spherules.

Exemplary oils or waxes which can be employed in the invention include mineral oils (liquid paraffin), plant oils (liquid fraction of shea butter, sunflower oil), synthetic oils, silicone oils or waxes (cyclomethicone), beeswax, carnauba wax or paraffin wax. To these oils fatty alcohols and fatty acids (stearic acid) can be added. Exemplary emulsifiers which can be employed in the invention include, for example, glycerol stearate, polysorbate 60 and the mixture PEG-6/PEG-32/Glycol Stearate sold under the name Tefose 63 by the company Gattefosse.

Exemplary solvents which may be employed in the invention include the lower alcohols, in particular ethanol and isopropanol, and propylene glycol. Exemplary hydrophilic gelling agents which may be employed in the invention include carboxyvinyl polymers (carbomers), acrylic copolymers such as acrylate/alkylacrylate copolymers, polyacrylamides, polysaccharides such as hydroxypropylcellulose, natural gums and clays, and exemplary lipophilic gelling agents include modified clays such as bentones, metal salts of fatty acids such as aluminum stearates, hydrophobic silica, ethylcellulose and polyethylene.

A composition of the invention can also comprise one or more other active agents, for example for preventing or combatting the appearance of signs of skin aging (cosmetic composition), or for preventing and/or treating pathologies associated with MMP-9 overexpression and/or hyperactivity (pharmaceutical composition). Pathologies associated with MMP-9 overexpression and/or hyperactivity are, for example, diseases of the skin, preferably selected from inflammatory diseases of the skin such as psoriasis, skin tumors such basal cell carcinoma, skin lesions such as chronic wounds, cicatrization pathologies, bullous dermatoses such as bullous pemphigoid, noninfectious granulomatous diseases such as sarcoidosis of the skin, granuloma annulare and necrobiosis lipedema, and skin pathologies related to exposure to ultraviolet solar rays, such as melanoma. Other non-limiting examples of pathologies associated with MMP-9 overexpression and/or hyperactivity are tumor pathologies, asthma, pulmonary emphysema, silicosis, bronchiectasis, anaphylactoid purpura, acute respiratory distress syndrome (ARDS), rheumatoid arthritis, periodontitis, inflammatory intestinal diseases, lupus nephritis, Sjögren syndrome, giant-cell arteritis, aneurism, peripheral nerve damage, Alzheimer's disease, Guillain-Barré syndrome, cystic fibrosis, and meningitis.

The aforesaid active agents which can be employed in combination with the aptamers according to the invention to prevent or combat the appearance of signs of skin aging, used pure or from extracts containing these molecules, are in particular, but are not limited to, the following compounds: UV filters (physical or chemical), retinol, retinol esters such as retinol propionate or retinol palmitate, beta-ecdysone, antioxidants or anti-inflammatory agents such as ascorbic acid or derivatives thereof such as ascorbyl-2-glucoside or 3-O-ethyl ascorbyl, tocopherol derivatives such as tocopheryl phosphate or potassium ascorbyl tocopheryl phosphate, dipotassium glycyrrhizinate and asiaticoside.

The present invention also has as an object the use of at least one aptamer according to the invention in a cosmetic composition for treating or preventing the appearance of signs, visible or not, of intrinsic and/or extrinsic skin aging or for slowing or attenuating the effects thereof, in particular for controlling skin remodeling, restructuring the epidermis, toning up the skin, and/or for preventing or promoting the smoothing or resorption of wrinkles.

The expression "skin aging" is considered here in its broadest meaning. It is associated with at least one condition selected from disintegration of collagen fiber bundle structure, formation of wrinkles, loss of skin elasticity, changes in skin texture, and decrease in the difference between a furrow and a rise of the skin surface.

More particularly, by "intrinsic aging," also known as "normal" or chronobiological aging, is meant here physiological changes at the molecular, cellular and/or tissular level of a subject related to programmed senescence involving endogenous factors. This intrinsic aging causes in particular slowing of the renewal of skin cells, keratinocytes, which is reflected primarily by the appearance of clinical changes such as a decrease in subcutaneous adipose tissue and the appearance of fine lines or wrinkles, and by histopathological changes such as an increase in the number and thickness of elastic fibers, a loss of vertical fibers of the membrane of elastic tissue, and the presence of large irregular fibroblasts in the cells of this elastic tissue.

By "extrinsic aging" is meant here physiological changes at the molecular, cellular and/or tissular level of a subject related to external stimulations such as excessive chemical and physical stimulations. Chemical and physical stimulations that can degrade the normal functions of the skin and induce skin aging include in particular exposure to the sun, to light, to UVs, stress and malnutrition. This extrinsic aging results in clinical changes such as deep wrinkles and the formation of skin having lost its firmness, its suppleness and its elasticity. These transformations are due primarily to histopathological changes, such as an excessive change in elastic tissue in the upper dermis and quantitative and qualitative degeneration of collagen fibers.

By "skin remodeling," or skin restructuring, is meant the concerted action of the enzymes involved in the degradation and synthesis of extracellular matrix of skin cells, such as cells of the epidermis, dermis and/or hypodermis. Indeed, the enzymes involved in extracellular matrix degradation regulate both degradation of extracellular matrix but also its synthesis in order to create a suitable environment allowing cell differentiation, proliferation or migration. The aptamer according to the invention makes it possible here to control this skin remodeling by protecting epidermal and/or dermal and/or hypodermal extracellular matrices.

The present invention also relates to the use of at least one aptamer according to the invention in or for the manufacture of a cosmetic or pharmaceutical composition as MMP-9 inhibitor.

The present invention also relates to the use of at least one aptamer according to the invention, in an anti-wrinkle cosmetic composition.

The present invention further relates to the use of at least one aptamer according to the invention for the manufacture of an anti-wrinkle dermatological composition.

Another object of the invention relates to the cosmetic use of an aptamer according to the invention, preferably for treating or preventing the appearance of signs, visible or not, of intrinsic and/or extrinsic skin aging or for slowing or attenuating the effects thereof, in particular for controlling skin remodeling, for restructuring the skin, for toning up the skin, and/or for preventing or promoting the smoothing or resorption of wrinkles.

In particular, the cosmetic use according to the invention has as an aim to smooth fine lines and wrinkles, in particular those appearing on the face, neck, low neckline or hands.

The present invention also relates to a method of cosmetic or dermatological treatment for treating or preventing the appearance of signs, visible or not, of intrinsic and/or extrinsic skin aging or for slowing or attenuating the effects thereof, in particular for controlling skin remodeling, for restructuring the skin, for toning up the skin, and/or for preventing or promoting the smoothing or resorption of wrinkles and/or for limiting the development of adipose tissue, consisting in applying to a relevant area of skin of the body or face a cosmetic or dermatological composition comprising at least one aptamer according to the invention.

Preferably, the composition of the invention is applied one once per day to the relevant area(s) of skin. Advantageously, the composition is applied a first time and again at night, to the same areas.

The present invention also relates to the use of at least one aptamer according to the invention for the manufacture of a medicinal product for simultaneous, separate or sequential administration in combination with one or more other active agents, for example the active agents described above.

The present invention also relates to the use of at least one aptamer according to the invention for the manufacture of a medicinal product for treating and/or preventing pathologies associated with MMP-9 overexpression and/or hyperactivity, said pathologies being preferably selected from those described above. More preferably, said pathologies are skin diseases such as those described above.

Another object of the invention relates to an aptamer according to the invention as medicinal product, preferably for treating and/or preventing pathologies associated with MMP-9 overexpression and/or hyperactivity, said pathologies being preferably selected from those described above. More preferably, said pathologies are skin diseases such as those described above.

Another object of the invention relates to an aptamer according to the invention for use in treating and/or preventing pathologies associated with MMP-9 overexpression and/or hyperactivity, said pathologies being preferably selected from those described above. More preferably, said pathologies are skin diseases such as those described above.

The aptamers according to the invention can be used in vectorized form, i.e., linked to a vector or a combination of vectors, in particular to facilitate their penetration in skin cells. This type of vector is well-known to the person skilled in the art. Examples of such vectors include, but are not limited to, liposomes, in particular cationic liposomes, hydrophobic residues such as cholesterol, dendrimers, in particular polycationic dendrimers, nanoparticles, microencapsulations, cell-penetrating peptides such as peptide transduction domains (PTDs), nucleic acid condensation agents such as polyethylene imine (PEI) or poly-L-lysine.

The aptamers according to the invention can also be used in the form of dimers of two aptamers or a conjugate of several aptamers.

The aptamers according to the invention can also be coupled to active agents for preventing or combatting skin aging or for treating and/or preventing skin diseases associated with MMP-9 overexpression and/or hyperactivity, for example the active agents described above.

Another object of the invention relates to a method for selecting an aptamer according to the invention comprising the following steps:
 selecting in an oligonucleotide library, using the SELEX method, aptamers against the catalytic site of MMP-9 protein,
 evaluating the potential to inhibit the enzymatic activity of MMP-9 protein of the aptamers identified in the preceding step,
 cloning and sequencing the aptamers thus selected.

According to a preferred embodiment of the invention, said aptamer library is a DNA library.

The present invention will be better understood in the light of the examples below. Nevertheless, the person skilled in the art will appreciate that the description above is not limiting and that various modifications, substitutions, omissions and changes can be made without leaving the scope of the invention.

EXAMPLES

Example 1

Selecting Anti-MMP9 Aptamers 1.1. Proteins

The catalytic domain of recombinant human MMP-9 containing a C-terminal 6-His tag was obtained from Biomol® International; MMP-9 and MMP-2 proteins were obtained from Calbiochem.

1.2. Oligonucleotides and library

Figure 1:
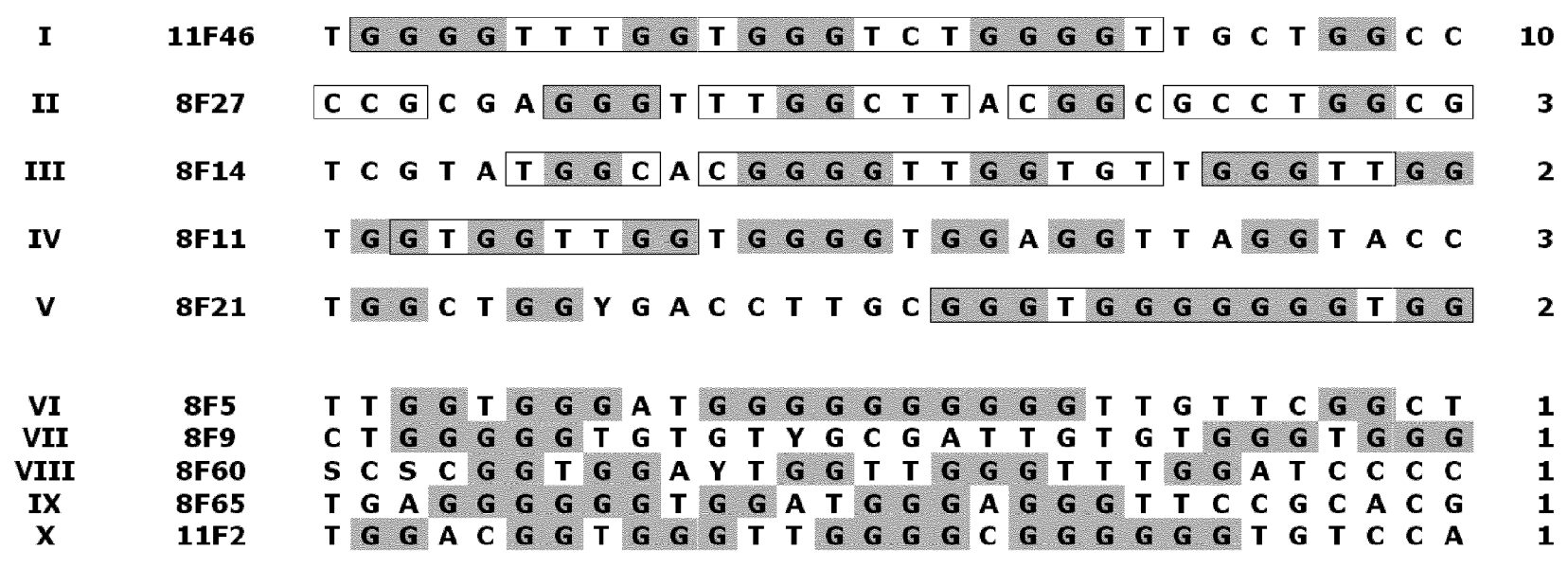

A DNA library and primers provided by Sigma were purified by HPLC. The primer sequences (P3) 5' GGGA-GACAAGAATAAACGCTCAA 3' (SEQ ID NO: 60) and (P5) 5' GCCTGTTGTGAGCCTCCTGTCGAA 3' (SEQ ID NO: 30) were used for amplification of the library containing a randomly selected 30-nucleotide window. The sequence 5' ACTGACTGACTGACTGACTA-6C3-GGGA-GACAAGAATAAACGCTCAA 3' (SEQ ID NO: 61) was used to produce the single strand as described in the literature (Williams and Bartel, 1995). The 5' biotinylated primer (P3) was used to produce single-stranded candidate DNAs. The candidate DNAs were synthesized and purified by HPLC by Eurogentec (FIGS. 1 and 2). Before every experiment the DNA populations and candidates were heated at 75° C. for 5 minutes, placed on ice for 5 minutes, and then placed at room temperature for at least 5 minutes.

1.3. In Vitro Selection

Before selection, the DNA library (1 nanomole) was treated and incubated with filters (0.45 µM HAWP, Millipore) twice for the first and second rounds and once for all the others rounds in PBS (50 mM Tris-HCl, pH 7.4, 50 mM NaCl, 100 mM KCl, 5 mM $CaCl_2$, 1 mM $(CH_3COO)_2Mg$) for 20 minutes at room temperature. In each round, an additional counter-selection was carried out against the 6-His-GST tag. Next, the counter-selected library was mixed with the catalytic domain of MMP-9 (20 picomoles) for 20 minutes and the unbound candidates were separated by means of the filter retention technique. After filtering, the candidates bound to the catalytic domain of MMP-9 were eluted by incubation for 20 minutes at 65° C. in 500 µl of 7 M phenol/urea, precipitated and amplified by PCR to produce the single strand used for the following rounds of selection. Reducing the amount of candidates and target during selection to reach 25 and 1 picomoles, respectively, in the eleventh round increased the stringency of the selection. Before cloning, the populations of each round of selection were evaluated for their ability to inhibit MMP-9 activity.

1.4. Cloning and Sequencing

After 11 rounds of selection, the sequences selected from rounds 8 and 11 were cloned using the TOPO MT Cloning Kit (Invitrogen) and sequenced using the BigDye Terminator v1.1 Cycle Sequencing Kit (Applied Biosystems) according to the manufacturers' instructions.

1.5. Thermal Denaturation of the DNA Aptamers

DNA aptamers were prepared in 20 mM sodium cacodylate buffer, pH 7.3 at 20° C., containing 140 mM potassium chloride, 20 mM sodium chloride and 3 mM magnesium chloride. DNA samples were prepared at final concentrations of 3 µM or 10 µM for the full-length and shortened candidates, respectively. The samples were denatured at 75° C. for 5 minutes, placed on ice for 5 minutes and incubated at room temperature for 20 minutes. Denaturation of the samples was carried out by means of heating of 0.4° C./min from 4 to 90° C. and was monitored at 260 and 295 nm. The thermal denaturation was monitored using a Uvikon spectrophotometer interfaced with a Peltier effect device which controls the temperature at ±0.1° C.

1.6. Circular Dichroism of the DNA Aptamers

CD spectra were obtained on a JASCO J-815 circular dichroism spectrometer using quartz cells with an optical pitch of 10-mm. Scans were carried out at 23° C., with a response time of 0.5 s, a scan speed of 500 nm/min and a wavelength range of 230-320 nm. A baseline for the buffer's contribution to the signal was subtracted from each spectrum.

The oligonucleotides were prepared at 0.5 and 1 µM for the full-length and shortened aptamers, respectively. They were heated in 70° C. water for 5 minutes, cooled at 4° C. for 4 minutes and stored at room temperature for 15 minutes in cacodylate buffer (20 mM sodium cacodylate, 140 mM KCl, 20 mM NaCl, 3 mM MgCl) until the analysis.

1.7. Results of the Selection of Anti-MMP-9 Aptamers

The SELEX method was used against the catalytic domain of MMP-9 in order to identify DNA aptamers that specifically inhibit enzymatic activity. Eleven rounds of in vitro selection were carried out. Before cloning and sequencing, the populations (starting with the library in round 11) were evaluated for their potential to inhibit MMP-9 activity.

On the basis of these activity tests, the populations from rounds 8 and 11 were cloned and sequenced.

The majority of the sequences have clusters of G which can produce G-quartets. Candidates were classified in five principal families (I, II, III, IV, V), each family containing sequences with a consensus motif (see the nucleotides enclosed in boxes in FIG. 1). The other sequences (8F5, 8F9, 8F60, 8F65 and 11F2) (group VI to X) have no similarity with the preceding families except for their richness in G.

Example 2

Measuring MMP-9 Activity 2.1. Principle

An enzyme is a protein that can specifically catalyze the transformation of one or two substrates. Taking a simplified enzymatic reaction model:

$$S \xrightarrow{E} P,$$

reaction rate is written:

$$v = \frac{d(P)}{dt} = -\frac{d(S)}{dt}.$$

To plot a (P)=ƒ(i) curve, the enzyme (E) acts on the substrate (S); time zero corresponds to triggering of the reaction. Appearance of the product (P) is measured as a function of time.

The reaction rate $$v = \frac{d(P)}{dt}$$

is constant during the initial conditions. For this portion of the curve, the tangent through the origin merges with the curve: the rate, with is the slope of the tangent, is called the initial rate. Then rate then decreases and becomes zero. The rate becomes zero when one of the substrates is consumed or when equilibrium is established.

When the rate of an enzymatic reaction is determined, it is always the initial rate that is calculated. Rate measurements are thus made under the initial conditions wherein less than 10% of the amount of substrate is hydrolyzed. While [S] ≫ [E], the initial rate is proportional to enzyme concentration: it thus reflects the activity of an enzyme preparation expressed in enzyme units. The international unit (IU or U) represents the amount of enzyme that catalyzes the transformation of a micromole of substrate per minute.

2.2. Measuring Enzymatic Activity

Measurement of the enzymatic activity of MMPs is based on the principle of resonance energy transfer, RET, or fluorescence resonance energy transfer, FRET. The substrate consists of an oligopeptide comprising a fluorescent group (F), energy donor, and a quenching group (Q), energy acceptor. After hydrolysis, the quenching group is released, making it possible to measure the increase in fluorescence.

Many fluorophore/quencher pairs have been developed for measuring the enzymatic activity of MMPs, including the pair 7-methoxycoumarin-4-acetyl (Mca)/dinitrophenyl-diaminopropionyl (Dnp) (Knight et al., 1991).

Measuring MMP activity in conditioned media

After incubation of the cells or 3D models in the presence of the various candidates or controls, the conditioned media are taken, centrifuged at 10,000 g for 10 minutes at +4° C. in order to remove cellular debris, and adjusted to the same protein concentration. Phenol red contained in the culture medium is removed by diafiltration using the Nanosep™ microconcentrator with a membrane having a 10 kDa cutoff. 50 µl of conditioned media is centrifuged at 14,000 g for 6 minutes at +4° C. The retentate is suspended in 50 µl of 50 mM Tris-HCl, 150 mM NaCl, 5 mM CaCl$_2$ buffer, pH 7.5, and centrifuged again under the same conditions. This step is repeated three times, thus completely removing the phenol red.

20 µl of media conditioned without phenol red is added to 170 µl of 50 mM Tris-HCl, 150 mM NaCl, 5 mM CaCl$_2$ buffer, pH 7.5, in a black 96-well plate the non-specific bindings sites of which have been blocked using a solution of 0.1% (w/v) bovine serum albumin (BSA) in 50 mM Tris-HCl, 150 mM NaCl, 5 mM CaCl$_2$ buffer, pH 7.5. The reaction is triggered by adding 10 µl of Mca-Pro-Leu-Gly-Leu-(Dnp)-Ala-Arg-NH$_2$ substrate at the final concentration of 2 µM in a final reaction volume of 200 µl. Variations in fluorescence (excitation wavelength: 326 nm, emission wavelength: 465 nm) over time are monitored using a BMG Polarstar plate reader spectrofluorometer at +20° C. The curve representing fluorescence (in RFU) as a function of time (in minutes) is plotted.

The initial rate of the reaction is determined by calculating the slope of the tangent through the origin. The ratio $V_i/V_o$ is calculated.

2.3. Modulation of MMP Activity in the Presence of Effector

Activation of proMMP-9 proMMP-9 is activated by incubation for 18 hours at +4° C. in the presence of 1 mM phenylmercuric acetate acid (PMAA), prepared at the concentration of 10 mM in 0.1 M soda.

Measuring Activity 200 pM MMP-9 is preincubated at +20° C. for 5 minutes in the absence or presence of the various candidates in 50 mM Tris-HCl, 150 mM NaCl, 5 mM CaCl$_2$ buffer, pH 7.5, in a black 96-well plate the non-specific bindings sites of which have been blocked using a solution of 0.1% (w/v) BSA in the same buffer. The reaction is triggered by adding 10 µl of specific substrate at the final concentration of 2 µM in a final reaction volume of 200 µl. Variations in fluorescence (excitation wavelength: 326 nm, emission wavelength: 465 nm) over time are monitored using a BMG Polarstar reader spectrofluorometer at +20° C. The curve representing fluorescence (in RFU) as a function of time (in minutes) is plotted.

The initial rate of the reaction is determined by calculating the slope of the tangent through the origin. The ratio $V_i/V_o$ is calculated.

2.4. Results

The results are represented in FIGS. 4 to 6. In FIGS. 5 and 6, a dose-dependent effect can be observed, the dose being indicated in nanomolar concentration on the abscissa after the name of the aptamer.

Example 3

Compositions According to the Present Invention 3.1. Example A: Cosmetic Powder for Lightening the Complexion of the Face

| | |
|---|---|
| Microcellulose | 20.00% |
| Sodium lauryl sulfoacetate | 15.00% |

| | |
|---|---|
| Aptamer according to the invention | 0.01% |
| Fragrance, colorants, preservatives | qs |
| Talc | qs to 100% |

This powder has a dual action. It cleanses the skin and, moreover, by regular use for several days, lightens the complexion. It can be applied to the skin of the face once or twice a day.

3.2. Example B: Cosmetic Antiaging Day Cream in Emulsion-Gel Form

| | |
|---|---|
| Glycerin | 5.00% |
| Caprylic/capric/succinic triglycerides | 5.00% |
| Octyl methoxycinnamate | 7.50% |
| Butyl methoxydibenzoyle methane | 2.00% |
| Dimethicone copolyol | 0.50% |
| Sodium hyaluronate | 0.1% |
| Acrylates/C10-30 alkyl acrylate crosspolymer | 0.50% |
| Aptamer according to the invention | 0.01% |
| Extract of mallow | 3% |
| Neutralizer | qs |
| Preservatives, fragrance, colorants | qs |
| Water | qs to 100% |

Some people exposed to relatively intense daylight radiation, or even direct sunlight, wish to protect themselves therefrom and to avoid solar elastosis. Use of the emulsion-gel of Example B makes it possible to achieve this aim. This composition is applied to the face, preferably in the morning. It acts both to prevent and to treat photoaging, uniform or not, of the face.

3.3. Example C: Cosmetic Liquid Sunscreen Composition (SPF 30)

| | |
|---|---|
| Volatile pentacyclomethicone | 49.00% |
| Titanium dioxide | 15.00% |
| Octyl methoxycinnamate | 7.50% |
| Glycerin | 5.00% |
| Phenyltrimethicone | 5.00% |
| Dimethicone copolyol | 3.00% |
| Polymethyl methacrylate | 2.50% |
| Butyl methoxydibenzoyle methane | 1.00% |
| Aptamer according to the invention | 0.01% |
| Neutralizer, fragrance, preservatives, antioxidants | qs |
| Water | qs to 100% |

This composition is to be used before exposure to intense sunlight. It prevents the appearance of wrinkles in people predisposed to this phenomenon.

3.4. Example D: Dermatological Antiaging Night Cream

| | |
|---|---|
| Glyceryl stearate + Peg-100 stearate | 5.00% |
| Hydrogenated polyisobutene | 4.00% |
| Magnesium ascorbyl phosphate | 3.00% |
| Tricaprylate/glycerol caprate | 3.00% |
| Squalane | 3.00% |
| Glycerin | 3.00% |
| Shea butter | 1.50% |
| Cetearyl octanoate | 1.50% |
| Ergothioneine | 0.50% |
| Cetyl alcohol | 1.00% |
| Stearyl alcohol | 1.00% |
| Dimethicone | 1.00% |
| Xanthan gum | 0.30% |
| Citric acid | 0.10% |
| Sodium citrate | 0.10% |
| Aptamer according to the invention | 0.001% |
| Adenosine | 1.00% |
| Neutralizer, fragrance, preservatives | qs |
| Water | qs to 100% |

Use of this cream smooths fine lines and wrinkles by means of collagen synthesis, its antioxidant action, and protection of extracellular matrix. This cream also attenuates contrasts in skin color that appear with age.

3.5. Example E: Cosmetic Antiaging Face Lotion

| | |
|---|---|
| Ethyl alcohol | 5.00% |
| PPG-3 Myristyl ether | 1.00% |
| Glycerin | 3.00% |
| Carbomer | 0.20% |
| Polysorbate 20 | 0.20% |
| Sodium tocopheryl phosphate | 0.1% |
| Biosaccharide gum 4 | 0.1% |
| Aptamer according to the invention | 0.0001% |
| Soy extract | 0.50% |
| Sodium polyacrylate | 0.50% |
| Neutralizer, fragrance, preservatives | qs |
| Water | qs to 100% |

This lotion, which fights skin aging and sagging, is used after removing make-up and cleansing the skin.

3.6. Example F: Cosmetic Antiaging Serum for the Face

| | |
|---|---|
| Water | qs to 100% |
| Glycerin | 5.00% |
| Tetrasodium EDTA | qs to desired pH |
| Citric acid | |
| Trisodium citrate | |
| Xanthan gum | 0.25% |
| Polyacrylamide, C13.14 isoparaffin, laureth-7 | 0.50% |
| Dimethicone copolyol | 0.25% |
| Aptamer according to the invention | 1.00% |
| Adenosine | 1.00% |
| Extract of mallow | 3.00% |
| Sodium hyaluronate | 0.10% |
| Tocopheryl acetate | 0.20% |
| Polysilicone 11 | 1.00% |
| Pentacyclomethicone | 4.00% |
| Fragrance, dye, preservative | qs |

A drop of this highly concentrated serum composition is applied to the face preferably before applying face cream. This serum is preferably used in a one- or two-week treatment for rejuvenating and smoothing the complexion.

3.7. Example G: Cosmetic Antiaging Gel Cream for the Hands

| | |
|---|---|
| Caprylic/capric diglyceryl succinate | 6% |
| Octyl octanoate | 2.5% |
| Octyl methoxycinnamate | 6% |
| Aptamer according to the invention | 0.1% |
| Phenyltrimethicone | 2.5% |
| Benzophenone-3 | 0.5% |
| Boron nitride | 1.00% |
| Camelia oil | 1% |
| Sodium hyaluronate | 0.05% |
| Xanthan gum | 0.2% |
| Acrylates/C10.30 alkyl acrylate copolymer | 0.5% |
| Glycerin | 7% |
| PEG 150 | 3% |
| Neutralizers, colorants, fragrance, preservatives | qs |
| Purified water | qs to 100% |

This anti-UV hand cream prevents the appearance of wrinkles and smooths the skin surface.

REFERENCES

Inomata S et al., J. Invest. Dermatol., 2003, 120, 128-134.
Bertin et al., Journal of Medicinal Chemistry, 2005, Vol. 48, No. 24.
Lateef et al., American Journal of Pathology, Vol. 165, No. 1, July 2004.
Williamson et al., Cell, 1989, 59(5): 871-80.
Sundquist and Klug, Nature, 1989, 342(6251): 825-9.
Tucker et al., Curr Pharm Des., 2012, 18(14):2014-26.
Folgueras et al, Int. J. Dev. Biul., 2004, 48: 411-424.
Chaussain-Miller et al, J Dent Res., 2006, 85, 22-32.
Knight et al., Biochem J., 1991 Feb. 15; 274 (Pt 1):45-8.
Knight et al., FEBS Lett., 1992 Jan. 27; 296(3):263-6.
Williams and Bartel, Nucleic Acids Res. 1995; (20) 4220-21.

The invention claimed is:

1. A method of using a cosmetic composition for treating the appearance of skin aging or for slowing or attenuating the effects thereof comprising topically administering a cosmetic composition comprising a G-quadruplex-structured aptamer capable of inhibiting the enzymatic activity of MMP-9 protein, wherein the aptamer is a DNA aptamer comprising at least one nucleotide sequence selected from the group consisting of the sequences SEQ ID NO: 1 to SEQ ID NO: 4.

2. The method of claim 1, wherein the aptamer is resistant to nucleases.

3. The method of claim 1, wherein the nucleotide sequence comprises at least 1 to 24 contiguous nucleotides of the sequence SEQ ID NO: 30 flanked at its 5' end, and/or at least 1 to 23 contiguous nucleotides of the sequence SEQ ID NO: 31 flanked at its 3' end.

4. A method of using a cosmetic composition for treating the appearance of skin aging or for slowing or attenuating the effects thereof comprising topically administering a cosmetic composition comprising a G-quadruplex-structured aptamer capable of inhibiting the enzymatic activity of MMP-9 protein, wherein the aptamer is a DNA aptamer comprising at least one nucleotide sequence selected from the group consisting of the sequences SEQ ID NO: 32 to SEQ ID NO: 59.

5. A method of using a composition comprising a G-quadruplex-structured aptamer capable of inhibiting the enzymatic activity of MMP-9 protein, wherein the aptamer is a DNA aptamer comprising at least one nucleotide sequence selected from the group consisting of the consensus sequences SEQ ID NO: 1 to SEQ ID NO: 4 for-treating pathologies associated with MMP-9 overexpression and/or hyperactivity comprising administering said composition topically to a subject.

6. The method of claim 5, wherein said pathologies are skin diseases selected from inflammatory diseases of the skin, skin tumors, skin lesions, cicatrization pathologies, bullous dermatoses, noninfectious granulomatous diseases, granuloma annulare, necrobiosis lipedema, and skin damage related to ultraviolet rays.

7. A method of using a cosmetic composition for treating the appearance of skin aging or for slowing or attenuating the effects thereof comprising topically administering a cosmetic composition comprising a G-quadruplex-structured aptamer capable of inhibiting the enzymatic activity of MMP-9 protein, wherein the aptamer is a DNA aptamer comprising at least one nucleotide sequence selected from the group consisting of the sequences SEQ ID NO: 6 to SEQ ID NO: 29.

8. The method of claim 5, wherein said pathologies are skin diseases selected from psoriasis, basal cell carcinoma, chronic wounds, bullous pemphigoid, and sarcoidosis of the skin.

9. The method of claim 1, wherein the aptamer comprises at least one nucleotide sequence selected from the group consisting of the sequences SEQ ID NO: 11 to SEQ ID NO: 27 and SEQ ID NO: 32 to SEQ ID NO: 52.

10. The method of claim 2, wherein the aptamer comprises at least one nucleotide sequence selected from the group consisting of the sequences SEQ ID NO: 11 to SEQ ID NO: 27 and SEQ ID NO: 32 to SEQ ID NO: 52.

11. The method of claim 9, wherein the aptamer comprises at least 1 to 24 contiguous nucleotides of the sequence SEQ ID NO: 30 flanked at its 5' end, and/or at least 1 to 23 contiguous nucleotides of the sequence SEQ ID NO: 31 flanked at its 3' end.

12. The method of claim 10, wherein the aptamer comprises at least 1 to 24 contiguous nucleotides of the sequence SEQ ID NO: 30 flanked at its 5' end, and/or at least 1 to 23 contiguous nucleotides of the sequence SEQ ID NO: 31 flanked at its 3' end.

13. The method of claim 9, wherein the nucleotide sequence is selected from the group consisting of the sequences SEQ ID NO: 32 to SEQ ID NO: 52.

14. The method of claim 10, wherein the nucleotide sequence is selected from the group consisting of the sequences SEQ ID NO: 32 to SEQ ID NO: 52.

* * * * *